(12) United States Patent
deLong et al.

(10) Patent No.: US 7,470,787 B2
(45) Date of Patent: Dec. 30, 2008

(54) ISOQUINOLINE COMPOUNDS

(75) Inventors: Mitchell A. deLong, Raleigh, NC (US); Marcos L. Sznaidman, Durham, NC (US); Robert H. Oakley, Durham, NC (US); Allen E. Eckhardt, Durham, NC (US); Christine Hudson, Durham, NC (US); Jeffrey D. Yingling, Apex, NC (US); Michael Peel, Chapel Hill, NC (US); Thomas E. Richardson, Durham, NC (US); Claire Louise Murray, Chapel Hill, NC (US); Byappanahally N. Narasinga Rao, Chapel Hill, NC (US); Brian H. Heasley, Wake Forest, NC (US); Paresma R. Patel, San Diego, CA (US)

(73) Assignee: Aerie Pharmaceuticals, Inc., Research Triangle Park, NC (US)

( * ) Notice: Subject to any disclaimer, the term of this patent is extended or adjusted under 35 U.S.C. 154(b) by 24 days.

(21) Appl. No.: 11/485,172

(22) Filed: Jul. 11, 2006

(65) Prior Publication Data

US 2007/0142429 A1    Jun. 21, 2007

Related U.S. Application Data

(60) Provisional application No. 60/698,165, filed on Jul. 11, 2005.

(51) Int. Cl.
  *C07D 217/00* (2006.01)
  *C07D 401/00* (2006.01)
  *C07D 215/00* (2006.01)
(52) U.S. Cl. .................. 546/146; 546/148; 546/152
(58) Field of Classification Search ............ 546/146, 546/148, 152
See application file for complete search history.

(56) References Cited

U.S. PATENT DOCUMENTS

| | | | |
|---|---|---|---|
| 5,891,646 | A | 4/1999 | Barak et al. |
| 6,110,693 | A | 8/2000 | Barak et al. |
| 6,787,534 | B2 | 9/2004 | Haneda et al. |
| 7,329,684 | B2 | 2/2008 | Mjalli et al. |
| 7,345,158 | B2 | 3/2008 | Egashira et al. |
| 7,361,678 | B2 | 4/2008 | Mjalli et al. |
| 7,374,891 | B2 | 5/2008 | Shahbaz |
| 7,378,498 | B2 | 5/2008 | Worley et al. |
| 2004/0091946 | A1 | 5/2004 | Oakley et al. |
| 2005/0032125 | A1 | 2/2005 | Oakley et al. |
| 2005/0282805 | A1* | 12/2005 | Hangeland et al. ....... 514/230.5 |
| 2006/0270670 | A1 | 11/2006 | Chew et al. |
| 2007/0111983 | A1 | 5/2007 | Fong |
| 2007/0123561 | A1 | 5/2007 | Lee et al. |
| 2007/0129404 | A1 | 6/2007 | Hagihara et al. |
| 2007/0135499 | A1 | 6/2007 | deLong et al. |
| 2007/0149473 | A1 | 6/2007 | Chatterton et al. |
| 2007/0149548 | A1 | 6/2007 | Hellberg et al. |
| 2007/0173530 | A1 | 7/2007 | deLong et al. |
| 2007/0238741 | A1 | 10/2007 | Nagarathnam et al. |
| 2008/0021026 | A1 | 1/2008 | Kahraman et al. |
| 2008/0021217 | A1 | 1/2008 | Borchardt |
| 2008/0058384 | A1 | 3/2008 | Lee et al. |
| 2008/0096238 | A1 | 4/2008 | Sharif et al. |
| 2008/0125427 | A1 | 5/2008 | Sehon et al. |
| 2008/0139595 | A1 | 6/2008 | Schirok et al. |
| 2008/0153813 | A1 | 6/2008 | Chen et al. |
| 2008/0161297 | A1 | 7/2008 | Bosanac et al. |
| 2008/0167340 | A1 | 7/2008 | deLong et al. |

FOREIGN PATENT DOCUMENTS

| | | |
|---|---|---|
| EP | 0232569 | 8/1987 |
| EP | 0389995 | 10/1990 |
| EP | 1550660 | 7/2005 |
| JP | 2007236388 | 9/2007 |
| JP | 2007246466 | 9/2007 |
| WO | WO 01/53274 | 7/2001 |
| WO | WO 02/22576 | 3/2002 |
| WO | WO 02/32864 | 4/2002 |
| WO | WO 03/073999 | 9/2003 |
| WO | 03/080578 | 10/2003 |
| WO | WO 2005/020921 | 3/2005 |
| WO | WO 2005/035503 | 4/2005 |
| WO | WO 2005/037257 | 4/2005 |
| WO | WO 2006/041119 | 4/2006 |
| WO | WO 2007/008926 | 1/2007 |
| WO | WO 2007/008942 | 1/2007 |
| WO | 2007/060028 | 5/2007 |
| WO | 2007/076360 | 7/2007 |
| WO | 2007/076367 | 7/2007 |
| WO | 2007/142323 | 12/2007 |
| WO | 2008/011557 | 1/2008 |
| WO | 2008/011560 | 1/2008 |

(Continued)

OTHER PUBLICATIONS

Banker, G.S. et al., Modern Pharmaceutics, Marcel Dekker, Inc., New York, (1979) Chapters 9 and 10.

(Continued)

*Primary Examiner*—D. Margaret Seaman
*Assistant Examiner*—Nizal S Chandrakumar
(74) *Attorney, Agent, or Firm*—Michael Best & Friedrich LLP

(57) ABSTRACT

Isoquinoline compounds with G are provided that influence, inhibit or reduce the action of a G-protein receptor kinase. Pharmaceutical compositions including therapeutically effective amounts of the isoquinoline compounds and pharmaceutically acceptable carriers are also provided. Various methods using the compounds and/or compositions to affect disease states or conditions such as cancer, osteoporosis and glaucoma are also provided.

26 Claims, 9 Drawing Sheets

FOREIGN PATENT DOCUMENTS

| | | |
|---|---|---|
| WO | 2008/016016 | 2/2008 |
| WO | 2008/036459 | 3/2008 |
| WO | WO 2008/036540 | 3/2008 |
| WO | 2008/049000 | 4/2008 |
| WO | 2008/049919 | 5/2008 |
| WO | 2008/054599 | 5/2008 |
| WO | 2008/077057 | 6/2008 |
| WO | 2008/077550 | 7/2008 |
| WO | 2008/077551 | 7/2008 |
| WO | 2008/077552 | 7/2008 |
| WO | 2008/077553 | 7/2008 |
| WO | 2008/077554 | 7/2008 |
| WO | 2008/077555 | 7/2008 |
| WO | 2008/077556 | 7/2008 |
| WO | 2008/079880 | 7/2008 |
| WO | 2008/079945 | 7/2008 |

OTHER PUBLICATIONS

C.T.F.A. Cosmetic Ingredient Handbook, "Surfactants—Emulsifying Agents", Second Edition, The Cosmetic, Toiletry, and Fragrance Association, New York, Wenninger, J.A. et al., eds. (1992) 587-592.

Capdeville, R. et al., "Glivec (STI571, IMATINIB), A Rationally Developed, Targeted Anticancer Drug", Nature Reviews Drug Discovery (2002) 1:493-502.

Dancey, J. et al., "Issues and Progress with Protein Kinase Inhibitors for Cancer Treatment", Nature Reviews Drug Discovery (2003) 2:296-313.

Hackam, A.S. et al., "The Wnt Signaling Pathway in Retinal Degenerations", IUBMB Life (2005) 57(6):381-388.

Inouye, Y. et al., "The Absolute Configurations of TRANS-1,2-Cyclopropanedicarboxylic Acid and TRANS-2-Phenylcyclopropanecarboxylic Acid", Int'l. J. Org. Chem. (1964) 20(5):1695-1699.

Liljebris, C. et al., "Derivatives of 17- Phenyl-18,19,20-trinorprostaglandin F2α Isopropyl Ester: Potential Antiglaucoma Agents," J. Med. Chem. (1995) 38(2):289-304.

McCutcheon's, "Emulsifiers & Detergents", North American Edition (1994) vol. 1:236-239.

Oakley, R.H. et al. "The Cellular Distribution of Fluorescently Labeled Arrestins Provides a Robust, Sensitive and Universal Assay for Screening G Protein-Coupled Receptors," Assay and Drug Development Technologies (2002) 1(1-1):21-30.

Penmetsa, K.V. et al., "Development of Reversed-Phase Chiral HPLC Methods Using Mass Spectrometry Compatible Mobile Phases", J. Liquid Chroma. Rel. Tech. (2000) 23(6-10):831-839.

Penn, R.B. et al., "Pharmacological Inhibition of Protein Kinases in Intact Cells: Antagonism of Beta Adrenergic Receptor Ligand Binding by H-89 Reveals Limitations of Usefulness." J. Pharm. Exp. Ther. (1999) 288(2):428-437.

Shankar, G. et al., "Protein-kinase-specific inhibitors block Langerhans' cell migration by inhibiting interleukin-1α release", Immunology (1999) 96:230-235.

Stirewalt, D.L. et al., "The Role of FLT3 In Haematopoietic Malignancies", Nature Reviews Cancer (2003) 3:650-665.

Webster, F.X. et al., "Following the Course of Resolution of Carboxylic Acids by 13C NMR Spectrometry of Amine Salts" J. Org. Chem. (1982) 47(26):5225-5226.

Westra, J. et al., "p38 Mitogen-Activated Protein Kinase (MAPK) in Rheumatoid Arthritis", Mini-Reviews in Medicinal Chemistry (2006) 6(8):867-874.

Chen, P. et al., "Identification of novel and potent isoquinoline aminooxazole-based IMPDH inhibitors," Bioorg. Med. Chem. Lett. (2003) 13(7):1345-1348.

Westaway, S.M. et al., "N-tetrahydroquinolinyl, N-quinolinyl and N-isoquinolinyl biaryl carboxamides as antagonists of TRPV1," Bioorg. Med. Chem. Lett. (2006) 16:4533-4536.

* cited by examiner

Effect of 60 minute pre-incubation of GRK2 inhibitor on morphine-induced B-arrestin translocation of mu-opioid receptor

ISOQUINOLINE COMPOUNDS

CROSS REFERENCE TO RELATED APPLICATIONS

This application claims benefit of U.S. Provisional Patent Application No. 60/698,165, filed Jul. 11, 2005, which is incorporated herein by reference in its entirety.

BACKGROUND

1. Field of the Invention

The present invention relates to isoquinoline compounds that may affect the action of G protein-coupled receptor kinases in a cell and that are useful as therapeutic agents or with therapeutic agents. In particular, these compounds are useful in the treatment of eye diseases or ocular disorders such as glaucoma.

2. Background

A variety of hormones, neurotransmitters and biologically active substances control, regulate or adjust the functions of living bodies via specific receptors located in cell membranes. Many of these receptors mediate the transmission of intracellular signals by activating guanine nucleotide-binding proteins (G proteins) to which the receptor is coupled. Such receptors are generically referred to as G-protein coupled receptors (GPCRs) and include, among others, α-adrenergic receptors, β-adrenergic receptors, opioid receptors, cannabinoid receptors and prostaglandin receptors.

The G-protein coupled receptors play an important role in the regulation of various physiological functions. By way of example, GPCRs have been implicated in a number of disease states, including, but not limited to: cardiac indications such as angina pectoris, essential hypertension, myocardial infarction, supraventricular and ventricular arrhythmias, congestive heart failure, atherosclerosis, renal failure, diabetes, respiratory indications such as asthma, chronic bronchitis, bronchospasm, emphysema, airway obstruction, upper respiratory indications such as rhinitis, seasonal allergies, inflammatory disease, inflammation in response to injury, rheumatoid arthritis, chronic inflammatory bowel disease, glaucoma, hypergastrinemia, gastrointestinal indications such as acid/peptic disorder, erosive esophagitis, gastrointestinal hypersecretion, mastocytosis, gastrointestinal reflux, peptic ulcer, Zollinger-Ellison syndrome, pain, obesity, bulimia nervosa, depression, obsessive-compulsive disorder, organ malformations (for example, cardiac malformations), neurodegenerative diseases such as Parkinson's Disease and Alzheimer's Disease, multiple sclerosis, Epstein-Barr infection and cancer.

The balance between the initiation and the turn off of the intracellular signal, called desensitization, regulates the intensity and duration of the response of the receptors to stimuli such as agonists. Desensitization of agonist-occupied GPCRs results from their phosphorylation by specific kinases called G protein-coupled receptor kinases (GRKs) and the subsequent binding of arrestin proteins to phosphorylated receptors. Arrestins are a family of intracellular proteins that bind activated GPCRs, including those that have been agonist-activated, and especially those that have been phosphorylated by G protein-coupled receptor kinases. The binding of the arrestins prevents further stimulation of G proteins and downstream signaling pathways. When desensitization occurs, the mediation or regulation of the physiological function mediated or regulated by the G proteins to which the receptors are coupled is reduced or prevented. For example, when agonists are administered to treat a disease or condition by activation of certain receptors, the receptors become desensitized from the action of the GRKs such that agonist administration may no longer result in therapeutic activation of the appropriate receptors. At that point, administration of the agonist no longer enables sufficient or effective control of or influence on the disease or condition intended to be treated.

In view of the role of GRKs in the desensitization of GPCRs, there is a need in the art for agents that prevent or reduce the desensitization of the GPCRs by controlling or inhibiting the action of the corresponding GRKs.

SUMMARY

A compound according to Formula I is provided:

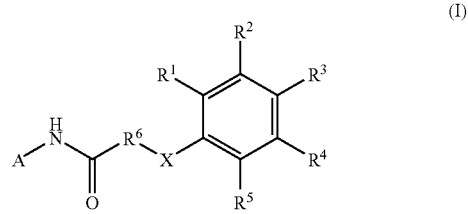

(I)

wherein A is a substituted or unsubstituted isoquinoline radical wherein the isoquinoline radical may be mono- or disubstituted with halogen, cyano, nitro or $C_1$-$C_4$ alkyl;

$R^1$, $R^2$, $R^3$, $R^4$, and $R^5$ are, independently selected from hydrogen; halogen; $C_1$-$C_4$ alkyl; alkoxy; amino; nitro; cyano; aryl; $C_1$-$C_4$ alkyl aryl; heteroaryl; $C_1$-$C_4$ alkyl heteroaryl; carbonylamino; thioalkyl; sulfonyl; sulfonylamino; acyl; or carboxyl;

R is $C_1$-$C_4$ alkyl, aryl, heteroaryl, $C_1$-$C_4$ alkyl aryl or $C_1$-$C_4$ alkyl heteroaryl;

X is O, S, S(O), S(O)(O),

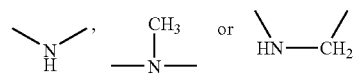

and $R^6$ is $CH_2$ or $CH(C_1$-$C_4$ alkyl).

An isoquinoline compound according to Formula II is further provided:

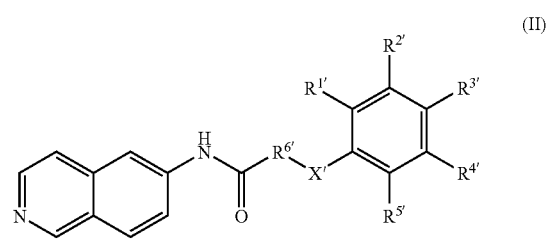

(II)

wherein $R^{1'}$, $R^{2'}$, $R^{3'}$, $R^{4'}$, and $R^{5'}$ are, independently, hydrogen; halogen; unsubstituted $C_1$-$C_4$ alkyl; amino; nitro; cyano; carbonylamino; alkoxy; —O—R; sulfonylamino; carboxyl; acyl; or thioalkyl;

R is $C_1$-$C_4$ alkyl, aryl, heteroaryl, $C_1$-$C_4$ alkyl aryl or $C_1$-$C_4$ alkyl heteroaryl;

X' is O, S, S(O), S(O)(O),

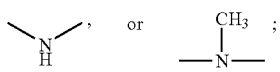

and

R⁶' is $CH_2$ or $CH(C_1-C_4$ alkyl).

In another embodiment, compositions comprising the compounds of formula (I) and a pharmaceutically acceptable carrier, as well as compositions comprising the compounds of formula (II) and a pharmaceutically acceptable carrier are provided.

In one embodiment, a pharmaceutical composition having GPCR desensitization inhibitory activity is provided for administration to a living organism, the pharmaceutical composition comprising a therapeutically effective amount of a compound according to Formula I or Formula II and a pharmaceutically acceptable carrier.

In a further embodiment, a method for influencing the action of a G-protein-coupled receptor kinase in a cell is provided comprising administering to or contacting with the cell at least one compound according to Formula (II). The method may be used to influence the action of a G-protein-coupled receptor kinase in a cell in vitro or in a cell in vivo in a living organism.

Another embodiment provides a method of reducing GPCR desensitization in a cell comprising administering to or contacting with the cell a therapeutically effective amount of a compound according to Formula (II). The method may be used to reduce GPCR desensitization in a cell in vitro or in a cell in vivo in a living organism.

A further embodiment provides a method of inhibiting the action of a G-protein-coupled receptor kinase comprising applying to a medium or contacting with a cell an effective inhibitory amount of a compound according to Formula (II). The method may be used to inhibit the action of a GRK in a cell in vitro or in a cell in vivo in a living organism.

An additional embodiment provides a method of treating a condition comprising administering to a subject in need of treatment a safe and effective amount of an isoquinoline derivative, wherein the condition is selected from the group consisting of eye disease, bone disorder (such as osteoporosis), heart disease, hepatic disease, renal disease, pancreatitis, cancer, myocardial infarct, gastric disturbance, hypertension, fertility control, nasal congestion, neurogenic bladder disorder, a gastrointestinal disorder, and a dermatological disorder. In one embodiment the condition comprises eye disease, and more particularly, glaucoma.

DETAILED DESCRIPTION

Figure 1:
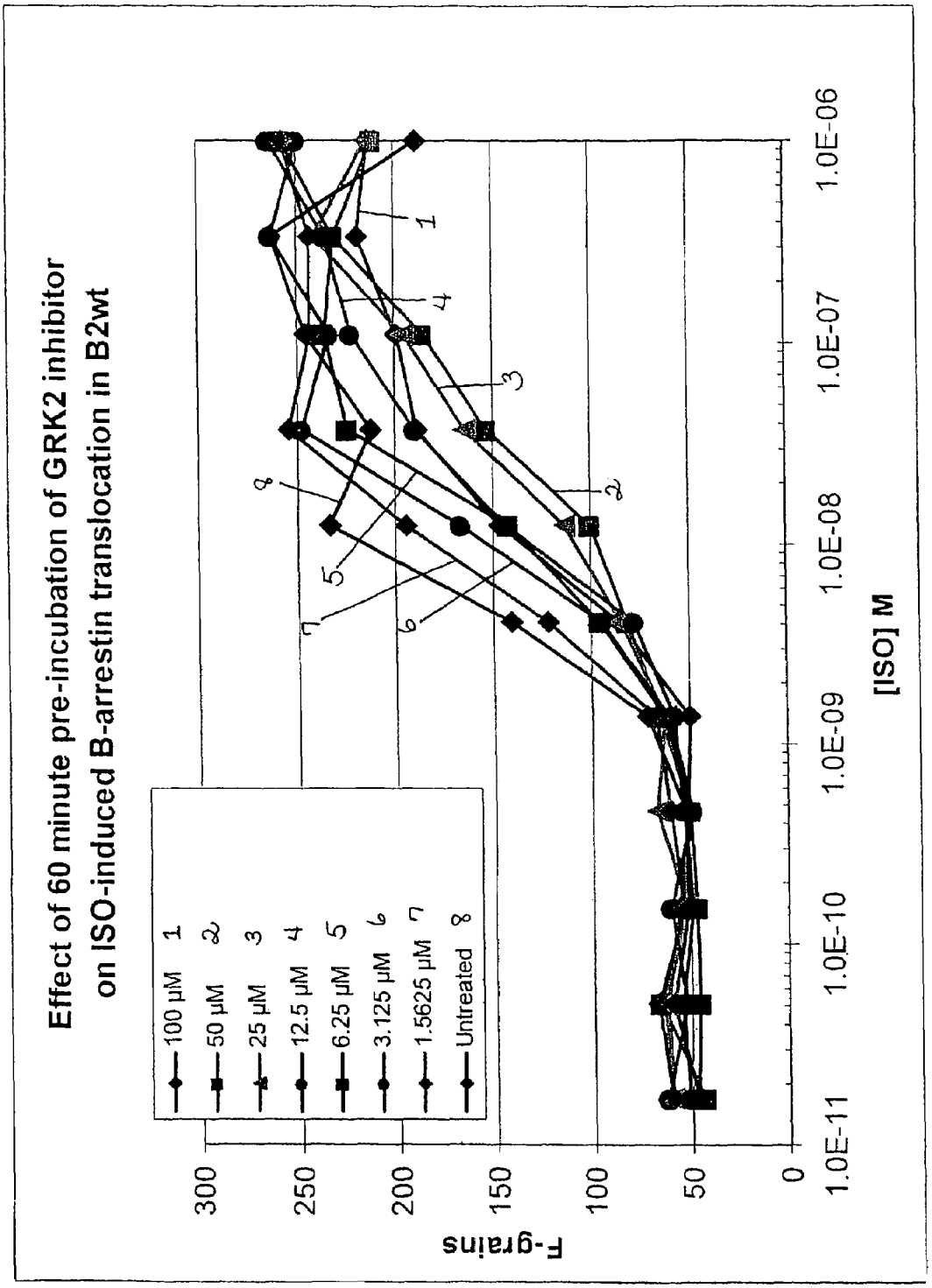
FIG. 1 is a graphical representation of the effect of a 60 minute pre-incubation of the GRK-2 inhibitor of Example 2 on ISO-induced β-arrestin translocation in β2 wt using a Transfluor® assay.

Novel isoquinoline compounds and methods of using those compounds to reduce or prevent desensitization of GPCR pathways are provided.

"Alkyl" refers to a saturated aliphatic hydrocarbon including straight chain and branched chain groups. "Alkyl" may be exemplified by groups such as methyl, ethyl, n-propyl, isopropyl, n-butyl and the like. Alkyl groups may be substituted or unsubstituted. When substituted, the substituent group is preferably amino, cyano, halogen, alkoxyl or hydroxyl. "$C_1$-$C_4$ alkyl" refers to alkyl groups containing one to four carbon atoms.

"Acyl" refers to the group —C(O)R wherein R is $C_1$-$C_4$ alkyl, aryl, heteroaryl, $C_1$-$C_4$ alkyl aryl or $C_1$-$C_4$ alkyl heteroaryl.

"Alkoxy" refers to the group —O-alkyl wherein alkyl has the definition given above.

"Carboxyl" refers to the group —C(=O)O—$C_1$-$C_4$ alkyl.

"Carbonylamino" refers to the group —C(O)NR'R' where each R' is, independently, hydrogen, $C_1$-$C_4$ alkyl, aryl, heteroaryl, $C_1$-$C_4$ alkyl aryl or $C_1$-$C_4$ alkyl heteroaryl.

"Aryl" refers to an aromatic carbocyclic group. "Aryl" may be exemplified by phenyl. The aryl group may be substituted or unsubstituted. When substituted, the substituent group is preferably amino, cyano, halogen, or hydroxyl.

"$C_1$-$C_4$ alkyl aryl" refers to $C_1$-$C_4$ alkyl groups having an aryl substituent such that the aryl substituent is bonded through the alkyl group. "$C_1$-$C_4$ alkyl aryl" may be exemplified by benzyl.

"$C_1$-$C_4$ alkyl heteroaryl" refers to $C_1$-$C_4$ alkyl groups having a heteroaryl substituent such that the heteroaryl substituent is bonded through the alkyl group.

"Halogen" refers to fluoro, chloro, bromo or iodo atoms.

"Heteroaryl" refers to a mono- or disubstituted monocyclic aromatic carbocyclic radical having one or more hetero atoms in the carbocyclic ring, wherein the substituents may be halogen, cyano, nitro or $C_1$-$C_4$ alkyl.

"Thioalkyl" refers to the group —S-alkyl.

"Sulfonyl" refers to the —S(O)$_2$R' group wherein R' is hydrogen, $C_1$-$C_4$ alkyl, aryl, heteroaryl, $C_1$-$C_4$ alkyl aryl or $C_1$-$C_4$ alkyl heteroaryl.

"Sulfonylamino" refers to the —S(O)$_2$NH— group.

"Pharmaceutically acceptable carrier" means a carrier that is useful for the preparation of a pharmaceutical composition that is generally compatible with the other ingredients of the composition, not deleterious to the recipient, and neither biologically nor otherwise undesirable. "A pharmaceutically acceptable carrier" includes both one and more than one carrier. Embodiments include carriers for topical, ocular, parenteral, intravenous, intraperitoneal intramuscular, sublingual, nasal and oral administration. "Pharmaceutically acceptable carrier" also includes agents for preparation of aqueous dispersions and sterile powders for injection or dispersions.

"Excipient" as used herein includes physiologically compatible additives useful in preparation of a pharmaceutical composition. Examples of pharmaceutically acceptable carriers and excipients can for example be found in Remington Pharmaceutical Science, 16$^{th}$ Ed.

"Therapeutically effective amount" as used herein refers to a dosage of the compounds or compositions effective for influencing, reducing, inhibiting or preventing desensitization of a receptor, particularly GPCR desensitization. This term as used herein may also refer to an amount effective at bringing about a desired in vivo effect in an animal, preferably, a human, such as reduction in intraocular pressure.

"Administering" as used herein refers to administration of the compounds as needed to achieve the desired effect.

"Eye disease" as used herein includes, but is not limited to, glaucoma, allergy and dry eye.

The term "disease or condition associated with G-protein receptor kinase activity" is used to mean a disease or condition resulting, in whole or in part, from the effect on GPCR(s) by one or more GRKs.

The term "controlling the disease or condition" is used to mean changing the effect on GPCR(s) by one or more GRKs to affect the disease or condition.

"Desensitization" or "GPCR desensitization" refers generally to the process by which sensitized GPCRs are converted to desensitized GPCRs.

"Desensitized GPCR" means a GPCR that presently does not have ability to respond to agonist and activate conventional G protein signaling.

"Sensitized GPCR" means a GPCR that presently has ability to respond to agonist and activate conventional G protein signaling.

"GPCR desensitization pathway" means any cellular component of the GPCR desensitization process, as well as any cellular structure implicated in the GPCR desensitization process and subsequent processes, including but not limited to, arrestins, GRKs, GPCRs, AP-2 protein, clathrin, protein phosphatases, and the like.

"GPCR signaling" means GPCR induced activation of G proteins. This may result in, for example, cAMP production.

"G protein-coupled receptor kinase" (GRK) includes any kinase that has the ability to phosphorylate a GPCR.

"GPCR desensitization inhibitory activity" of a composition (e.g., compound, solution, etc.) means that the composition is capable of inhibiting GPCR desensitization of at least one specific GPCR.

The term "to inhibit the G-protein receptor kinase activity" or "inhibit the action of a GRK" means to reduce or decrease the action of the GRK.

The term "to influence the GRK activity" or "to influence the action of the GRK" means to change or affect the action or activity of a GRK on one or more GPCRs.

The isoquinoline compounds may be represented by Formula I:

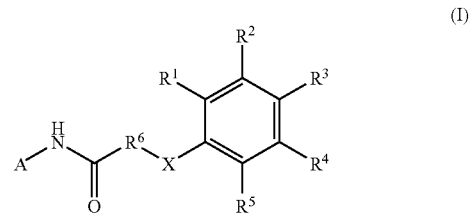

(I)

wherein A is a substituted or unsubstituted isoquinoline radical wherein the isoquinoline radical may be mono- or disubstituted with halogen, cyano, nitro or $C_1$-$C_4$ alkyl;

$R^1$, $R^2$, $R^3$, $R^4$, and $R^5$ are, independently, hydrogen; halogen; $C_1$-$C_4$ alkyl; alkoxy; phenoxy; —O—R; —SR; amino; nitro; cyano; aryl; $C_1$-$C_4$ alkyl aryl; heteroaryl; $C_1$-$C_4$ alkyl heteroaryl; carbonylamino; thioalkyl; sulfonyl; sulfonylamino; acyl; or carboxyl;

R is $C_1$-$C_4$ alkyl, aryl, heteroaryl, $C_1$-$C_4$ alkyl aryl or $C_1$-$C_4$ alkyl heteroaryl;

X is O, S, S(O), S(O)(O),

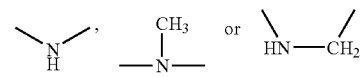

and $R^6$ is $CH_2$ or $CH(C_1$-$C_4$ alkyl).

In a preferred embodiment of Formula (I), A is an unsubstituted isoquinoline radical and $R^1$, $R^3$, and $R^5$ are hydrogen. In another preferred embodiment of Formula (I), X is

In another preferred embodiment of Formula (I), $R^1$, $R^3$, and $R^5$ are hydrogen and $R^2$ or $R^4$ is —O—R, as defined above.

In another embodiment, the isoquinoline compounds may be represented by Formula (II):

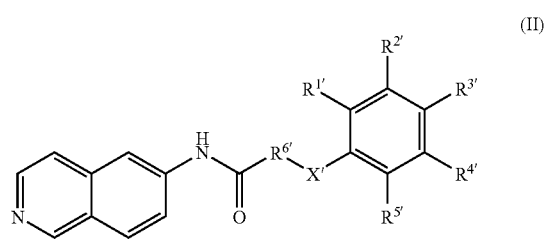

(II)

wherein $R^{1'}$, $R^{2'}$, $R^{3'}$, $R^{4'}$, and $R^{5'}$ are, independently, hydrogen; halogen; unsubstituted $C_1$-$C_4$ alkyl; amino; nitro; cyano; carbonylamino; alkoxy; —O—R; —SR; sulfonylamino; carboxyl; acyl; phenoxy or thioalkyl;

R is $C_1$-$C_4$ alkyl, aryl, heteroaryl, $C_1$-$C_4$ alkyl aryl or $C_1$-$C_4$ alkyl heteroaryl;

X' is O, S, S(O), S(O)(O),

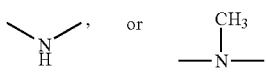

and

R$^{6'}$ is CH$_2$ or CH(C$_1$-C$_4$ alkyl).

In some preferred embodiments, the isoquinolines include those compounds wherein R$^{1'}$, R$^{3'}$ and R$^{5'}$ are hydrogen and X' is

In further preferred embodiments, one of R$^{2'}$ or R$^{4'}$ is also hydrogen. In some preferred embodiments either R$^{2'}$ or R$^{4'}$ is hydrogen and the other R$^{2'}$ or R$^{4'}$ group is —O-benzyl; cyano; —C(O)—NH-phenyl; hydrogen; —O-phenyl; —S—C$_1$-C$_4$ alkyl, preferably —S—CH$_3$; —C$_1$-C$_4$ alkyl, preferably methyl, —C(O)—NH-m-pyridine, —C(O—)NH$_2$, —SO$_2$—NH$_2$, —C(O)O—C$_1$-C$_4$ alkyl, preferably —C(O)O—CH$_3$; —C(O)phenyl; —C(O)NH—C$_1$-C$_4$ alkyl, preferably —C(O)NH—CH$_3$; halogen, preferably chlorine or fluorine; —C(O)—C$_1$-C$_4$ alkyl, preferably —C(O)—CH$_3$; or —O—C$_1$-C$_4$ alkyl, preferably O—CH$_3$ or O-propyl, preferably isopropyl. In some preferred embodiments R$^{2'}$ and R$^{4'}$ are hydrogen and R$^{3'}$ is selected from the group comprising —O-benzyl; cyano; —C(O)—NH-phenyl; hydrogen; —O-phenyl; —S—C$_1$-C$_4$ alkyl, preferably —S—CH$_3$; —C$_1$-C$_4$ alkyl, preferably methyl, —C(O)—NH-m-pyridine, —C(O—)NH$_2$, —SO$_2$—NH$_2$, —C(O)O—C$_1$-C$_4$ alkyl, preferably —C(O)O—CH$_3$; —C(O)aryl; —C(O)NH—C$_1$-C$_4$ alkyl, preferably —C(O)NH—CH$_3$; halogen, —C(O)—C$_1$-C$_4$ alkyl, preferably —C(O)—CH$_3$; or —O—C$_1$-C$_4$ alkyl, preferably O—CH$_3$ or O-propyl, preferably isopropyl.

The isoquinoline compounds may be synthesized by the general schemes set forth below:

Synthesis of Isoquinolines

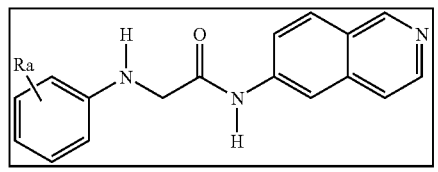

Scheme 1

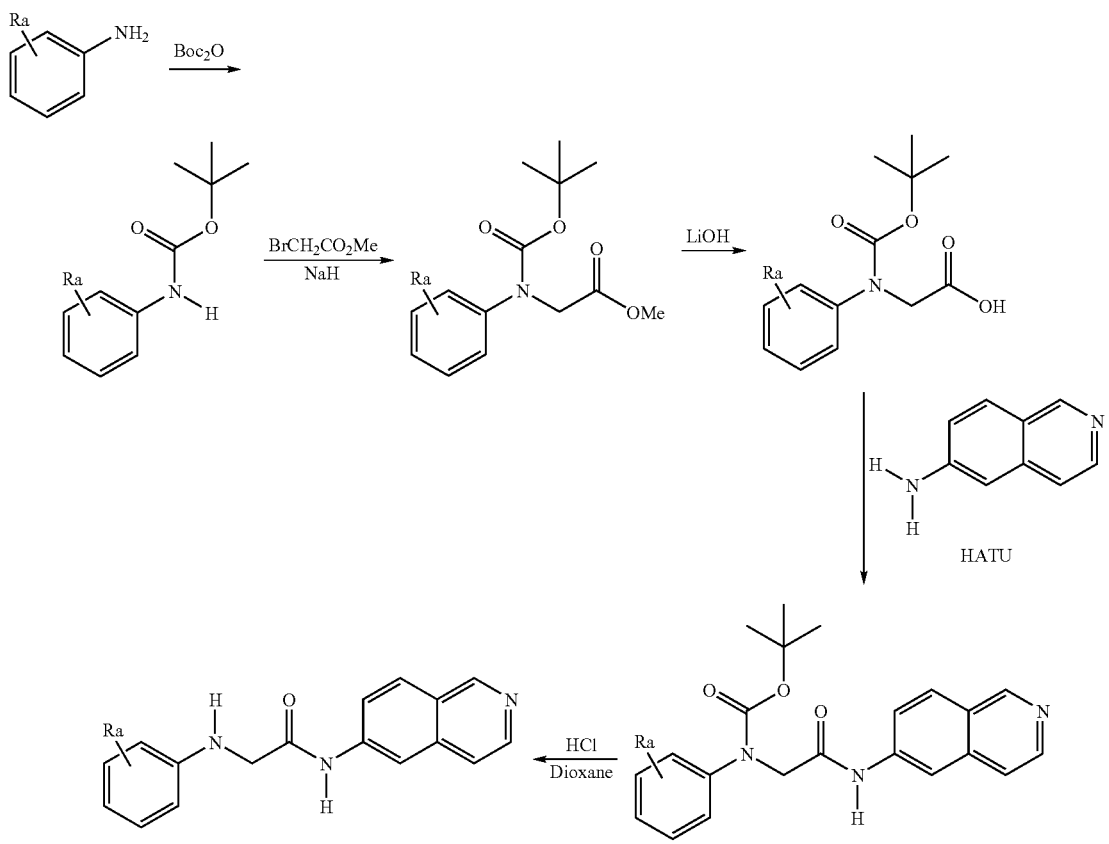

Scheme 1: The corresponding substituted aniline was treated with a suitable protecting group such as tert-butoxycarbonyl, followed by reaction with a suitable electrophile in a non-protic solvent in the presence of an appropriate base such as NaH. Saponification of the glycine ester derivative yields the appropriate carboxylic acid, which can be coupled to 6-aminoisoquinoline using standard amide coupling procedures to provide substituted aminoisoquinoline. Removal of the protecting group following established protocols for such transformations provides the final isoquinoline derivatives.

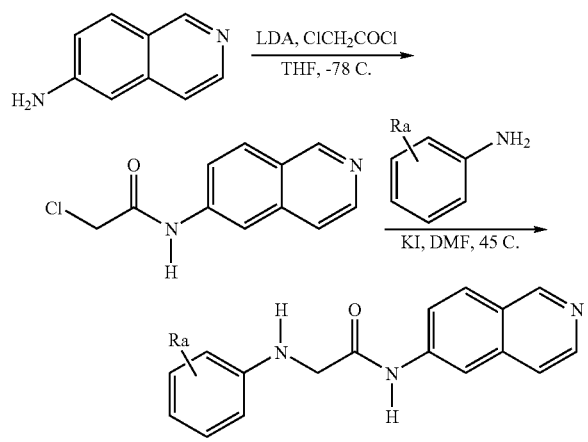

Scheme 2

Scheme 2: Alternatively, compounds of the invention may be prepared via the method described in Scheme 2. 6-Aminoisoquinoline can be acylated using the appropriate acylating agent in a non-protic solvent with an appropriate base. Use of LDA as the base and chloroacetyl chloride gives a chloroacetamide derivative. Treatment of this material with the corresponding substituted aniline in an appropriate solvent and optionally heating the reaction affords the final isoquinoline derivatives.

The $R^a$ group generally represents the substituents as set forth in either Formula I or Formula II for groups $R^1$, $R^2$, $R^3$, $R^4$, and $R^5$ or $R^{1'}$, $R^{2'}$, $R^{3'}$, $R^{4'}$, and $R^{5'}$. The abbreviations used in the synthesis schemes shown have the following meanings: $Boc_2O$ means di-tert-butyl-dicarbonate, HATU means 2-(7-Aza-1H-benzotriazole-1-yl)-1,1,3,3-tetramethyluronium hexafluorophosphate, LDA means lithium diisopropyl amide, DMF is dimethylformamide, and THF is tetrahydrofuran.

The isoquinoline compounds of Formula (I) or Formula (II) and compositions including them have GPCR desensitization inhibitory activity and may be useful in influencing or inhibiting the action of G-protein receptor kinases, influencing, preventing or reducing the desensitization of receptors phosphorylated by G-protein receptor kinases, influencing or inhibiting other GRK-mediated events and in treatment and/or prevention of diseases or conditions controlled by receptors affected by one or more of the G-protein receptor kinases. The isoquinolines may be used to influence or inhibit the action of GRKs either in a cell in vitro or in a cell in a living body in vivo. Specifically, in one embodiment, a method is provided of inhibiting the action of a G-protein-coupled receptor kinase comprising applying to a medium such as an assay medium or contacting with a cell either in a cell in vitro or in a cell in a living body in vivo an effective inhibitory amount of a compound according to Formula (I) or (II). In a preferred embodiment, the GRK inhibited is GRK-2, GRK-3, GRK-5 or GRK-6. In a further preferred embodiment, the GRK inhibited is GRK-2.

In one embodiment, the isoquinolines according to Formulas I or II are used in methods of reducing GPCR desensitization in a cell comprising administering to, or contacting with, the cell a therapeutically effective amount of one or more of the isoquinolines. The one or more of the isoquinolines are preferably administered in a pharmaceutically acceptable formulation, such as in or with a pharmaceutically acceptable carrier when the isoquinolines are administered to a cell or cells in a living organism or body. In another embodiment, the isoquinolines according to Formulas I or II are used in methods for influencing the action of a G-protein-coupled receptor kinase in a cell comprising administering to, or contacting with, the cell an effective amount of one or more isoquinolines for influencing the action of the GRK in the cell. The one or more of the isoquinolines are preferably administered in a pharmaceutically acceptable formulation, such as in or with a pharmaceutically acceptable carrier when the isoquinolines are administered to a cell or cells in a living organism or body.

Treatment or prevention of diseases or conditions for which the isoquinolines may be useful include any of the diseases or conditions associated with G-protein receptor kinase activity or diseases or conditions affected by GRK-mediated desensitization of GPCRs. By way of example, continuous exposure to endogenous stimuli can cause down-regulation and loss of response of beneficial GPCRs in certain hereditary as well as most chronic diseases. Examples of this type of disease behavior include the down-regulation and loss of response by both β-1 and β-2 adrenergic receptors in congestive heart failure. Desensitization via down-regulation of the receptors is also seen with exogenous administration of agonists or drugs such as morphine for pain or salbutamol for asthma, for example, in which desensitization of the receptors results in an undesired adverse effect known as drug tolerance. The isoquinolines may be used to influence or reduce the GRK-controlled desensitization for conditions affected by the action or activity of GRKs, resulting in a therapeutic effect.

The isoquinolines in some embodiments will be administered in conjunction with the administration of a therapeutic agent which is directed to influencing or controlling specific G-protein coupled receptors for the treatment or prevention of a condition or disease affected by those specific receptors. Combining administration of the isoquinolines with a GPCR-directed therapeutic agent will provide a reduction or prevention of desensitization of the receptors to which the therapeutic agent is directed, resulting in improving the ability of the therapeutic agent to have the desired effect over a longer period of time. Additionally, the administration of the therapeutic agent or receptor agonist with an isoquinoline formulation will enable lower doses of the therapeutic agent to be administered for a longer period of time.

One or more therapeutic agents may be administered with one or more isoquinoline compounds. The therapeutic agents and/or the isoquinoline compounds are preferably administered in a pharmaceutically acceptable formulation with a pharmaceutically acceptable carrier when the isoquinolines are administered to a cell or cells in a living organism or body.

Compositions including the isoquinolines of Formulae I or II may be obtained in the form of various salts or solvates. As the salts, physiologically acceptable salts or salts available as raw materials are used.

Pharmaceutical compositions for use in accordance with the present invention may be formulated in a conventional manner using one or more physiologically acceptable carriers or excipients. Thus, the compounds and their physiologically acceptable salts and solvates may be formulated for administration by, for example, eyedrop, in a topical oil-based formulation, injection, inhalation (either through the mouth or the nose), oral, buccal, parenteral or rectal administration. Techniques and formulations may generally be found in "Remington's Pharmaceutical Sciences", (Meade Publishing Co., Easton, Pa.). Therapeutic compositions must typically be sterile and stable under the conditions of manufacture and storage.

Compositions of the present invention may comprise a safe and effective amount of the subject compounds, and a pharmaceutically-acceptable carrier. As used herein, "safe and effective amount" means an amount of a compound sufficient to significantly induce a positive modification in the condition to be treated, but low enough to avoid serious side effects (at a reasonable benefit/risk ratio), within the scope of sound medical judgment. A safe and effective amount of a compound will vary with the particular condition being treated, the age and physical condition of the patient being treated, the severity of the condition, the duration of the treatment, the nature of concurrent therapy, the particular pharmaceutically-acceptable carrier utilized, and like factors within the knowledge and expertise of the attending physician.

The route by which the compounds of the present invention (component A) will be administered and the form of the composition will dictate the type of carrier (component B) to be used. The composition may be in a variety of forms, suitable, for example, for systemic administration (e.g., oral, rectal, nasal, sublingual, buccal, or parenteral) or topical administration (e.g., local application on the skin, ocular, liposome delivery systems, or iontophoresis).

Carriers for systemic administration typically comprise at least one of a) diluents, b) lubricants, c) binders, d) disintegrants, e) colorants, f) flavors, g) sweeteners, h) antioxidants, j) preservatives, k) glidants, m) solvents, n) suspending agents, o) wetting agents, p) surfactants, combinations thereof, and others. All carriers are optional in the systemic compositions.

Ingredient a) is a diluent. Suitable diluents for solid dosage forms include sugars such as glucose, lactose, dextrose, and sucrose; diols such as propylene glycol; calcium carbonate; sodium carbonate; sugar alcohols, such as glycerin; mannitol; and sorbitol. The amount of ingredient a) in the systemic composition is typically about 50 to about 90%.

Ingredient b) is a lubricant. Suitable lubricants for solid dosage forms are exemplified by solid lubricants including silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of ingredient b) in the systemic composition is typically about 5 to about 10%.

Ingredient c) is a binder. Suitable binders for solid dosage forms include polyvinylpyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of ingredient c) in the systemic composition is typically about 5 to about 50%.

Ingredient d) is a disintegrant. Suitable disintegrants for solid dosage forms include agar, alginic acid and the sodium salt thereof, effervescent mixtures, croscarmelose, crospovidone, sodium carboxymethyl starch, sodium starch glycolate, clays, and ion exchange resins. The amount of ingredient d) in the systemic composition is typically about 0.1 to about 10%.

Ingredient e) for solid dosage forms is a colorant such as an FD&C dye. The amount of ingredient e) in the systemic composition is typically about 0.005 to about 0.1%.

Ingredient f) for solid dosage forms is a flavor such as menthol, peppermint, and fruit flavors. The amount of ingredient f) in the systemic composition is typically about 0.1 to about 1.0%.

Ingredient g) for solid dosage forms is a sweetener such as aspartame and saccharin. The amount of ingredient g) in the systemic composition is typically about 0.001 to about 1%.

Ingredient h) is an antioxidant such as butylated hydroxyanisole ("BHA"), butylated hydroxytoluene ("BHT"), and vitamin E. The amount of ingredient h) in the systemic composition is typically about 0.1 to about 5%.

Ingredient j) is a preservative such as benzalkonium chloride, methyl paraben and sodium benzoate. The amount of ingredient j) in the systemic composition is typically about 0.01 to about 5%.

Ingredient k) for solid dosage forms is a glidant such as silicon dioxide. The amount of ingredient k) in the systemic composition is typically about 1 to about 5%.

Ingredient m) is a solvent, such as water, isotonic saline, ethyl oleate, alcohols such as ethanol, and phosphate buffer solutions. The amount of ingredient m) in the systemic composition is typically from about 0 to about 100%.

Ingredient n) is a suspending agent. Suitable suspending agents include AVICEL® RC-591 (from FMC Corporation of Philadelphia, Pa.) and sodium alginate. The amount of ingredient n) in the systemic composition is typically about 1 to about 8%.

Ingredient o) is a surfactant such as lecithin, polysorbate 80, and sodium lauryl sulfate, and the TWEENS® from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of ingredient o) in the systemic composition is typically about 0.1% to about 2%.

Although the amounts of components A and B in the systemic compositions will vary depending on the type of systemic composition prepared, the specific derivative selected for component A and the ingredients of component B, in general, system compositions comprise 0.01% to 50% of component A and 50 to 99.99% of component B.

Compositions for parenteral administration typically comprise A) 0.1 to 10% of the compounds of the present invention and B) 90 to 99.9% of a carrier comprising a) a diluent and m) a solvent. In one embodiment, component a) comprises propylene glycol and m) comprises ethanol or ethyl oleate.

Compositions for oral administration can have various dosage forms. For example, solid forms include tablets, capsules, granules, and bulk powders. These oral dosage forms comprise a safe and effective amount, usually at least about 5%, and more particularly from about 25% to about 50% of component A). The oral dosage compositions further comprise about 50 to about 95% of component B), and more particularly, from about 50 to about 75%.

Tablets can be compressed, tablet triturates, enteric-coated, sugar-coated, film-coated, or multiple-compressed. Tablets typically comprise component A, and component B a carrier comprising ingredients selected from the group consisting of a) diluents, b) lubricants, c) binders, d) disintegrants, e) colorants, f) flavors, g) sweeteners, k) glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain g) sweeteners such as aspartame and saccharin, or f) flavors such as menthol, peppermint, fruit flavors, or a combination thereof.

Capsules (including time release and sustained release formulations) typically comprise component A, and a carrier comprising one or more a) diluents disclosed above in a capsule comprising gelatin. Granules typically comprise component A, and preferably further comprise k) glidants such as silicon dioxide to improve flow characteristics.

The selection of ingredients in the carrier for oral compositions depends on secondary considerations like taste, cost, and shelf stability, which are not critical for the purposes of this invention. One skilled in the art would know how to select appropriate ingredients without undue experimentation.

The solid compositions may also be coated by conventional methods, typically with pH or time-dependent coatings, such that component A is released in the gastrointestinal tract in the vicinity of the desired application, or at various points and times to extend the desired action. The coatings typically comprise one or more components selected from the group consisting of cellulose acetate phthalate, polyvinyl acetate phthalate, hydroxypropyl methyl cellulose phthalate, ethyl cellulose, EUDRAGIT® coatings (available from Rohm & Haas G.M.B.H. of Darmstadt, Germany), waxes and shellac.

Compositions for oral administration can also have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically comprise component A and component B, namely, a carrier comprising ingredients selected from the group consisting of a) diluents, e) colorants, f) flavors, g) sweeteners, j) preservatives, m) solvents, n) suspending agents, and o) surfactants. Peroral liquid compositions preferably comprise one or more ingredients selected from the group consisting of e) colorants, f) flavors, and g) sweeteners.

Other compositions useful for attaining systemic delivery of the subject compounds include sublingual, buccal and nasal dosage forms. Such compositions typically comprise one or more of soluble filler substances such as a) diluents including sucrose, sorbitol and mannitol; and c) binders such as acacia, microcrystalline cellulose, carboxymethyl cellulose, and hydroxypropyl methylcellulose. Such compositions may further comprise b) lubricants, e) colorants, f) flavors, g) sweeteners, h) antioxidants, and k) glidants.

In one embodiment of the invention, the compounds of the present invention are topically administered. Topical compositions that can be applied locally to the eye may be in any form known in the art, non-limiting examples of which include gelable drops, spray, ointment, or a sustained or non-sustained release unit placed in the conjunctival cul-du-sac of the eye.

Topical compositions that can be applied locally to the skin may be in any form including solutions, oils, creams, ointments, gels, lotions, shampoos, leave-on and rinse-out hair conditioners, milks, cleansers, moisturizers, sprays, skin patches, and the like. Topical compositions comprise: component A, the compounds described above, and component B, a carrier. The carrier of the topical composition preferably aids penetration of the compounds into the eye. Component B may further comprise one or more optional components.

The dosage range of the compound for systemic administration is from about 0.01 to about 1000 µg/kg body weight, preferably from about 0.1 to about 100 µg/kg per body weight, most preferably form about 1 to about 50 µg/kg body weight per day. The transdermal dosages will be designed to attain similar serum or plasma levels, based upon techniques known to those skilled in the art of pharmacokinetics and transdermal formulations. Plasma levels for systemic administration are expected to be in the range of 0.01 to 100 nanograms/ml, more preferably from 0.05 to 50 ng/ml, and most preferably from 0.1 to 10 ng/ml. While these dosages are based upon a daily administration rate, weekly or monthly accumulated dosages may also be used to calculate the clinical requirements.

Dosages may be varied based on the patient being treated, the condition being treated, the severity of the condition being treated, the route of administration, etc. to achieve the desired effect.

The compounds of the present invention are also useful in decreasing intraocular pressure. Thus, these compounds are useful in the treatment of glaucoma. The preferred route of administration for treating glaucoma is topically.

The exact amounts of each component in the topical composition depend on various factors. The amount of component A added to the topical composition is dependent on the $IC_{50}$ of component A, typically expressed in nanomolar (nM) units. For example, if the $IC_{50}$ of the medicament is 1 nM, the amount of component A will be from about 0.0001 to about 0.01%. If the $IC_{50}$ of the medicament is 10 nM, the amount of component A) will be from about 0.001 to about 0.1%. If the $IC_{50}$ of the medicament is 100 nM, the amount of component A will be from about 0.01 to about 1.0%. If the $IC_{50}$ of the medicament is 1000 nM, the amount of component A will be 0.1 to 10%, preferably 0.5 to 5.0%. If the amount of component A is outside the ranges specified above (i.e., either higher or lower), efficacy of the treatment may be reduced. $IC_{50}$ can be calculated according to the method in Reference Example 1, below. One skilled in the art would know how to calculate an $IC_{50}$. The remainder of the composition, up to 100%, is component B.

The amount of the carrier employed in conjunction with component A is sufficient to provide a practical quantity of composition for administration per unit dose of the medicament. Techniques and compositions for making dosage forms useful in the methods of this invention are described in the following references: *Modern Pharmaceutics*, Chapters 9 and 10, Banker & Rhodes, eds. (1979); Lieberman et al., *Pharmaceutical Dosage Forms: Tablets* (1981); and Ansel, *Introduction to Pharmaceutical Dosage Forms*, $2^{nd}$ Ed., (1976).

Component B may comprise a single ingredient or a combination of two or more ingredients. In the topical compositions, component B comprises a topical carrier. Suitable topical carriers comprise one or more ingredients selected from the group consisting of phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols and symmetrical alcohols.

The carrier of the topical composition may further comprise one or more ingredients selected from the group consisting of q) emollients, r) propellants, s) solvents, t) humectants, u) thickeners, v) powders, w) fragrances, x) pigments, and y) preservatives.

Ingredient q) is an emollient. The amount of ingredient q) in a skin-based topical composition is typically about 5 to about 95%. Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane.

Ingredient r) is a propellant. The amount of ingredient r) in the topical composition is typically about 0 to about 95%. Suitable propellants include propane, butane, isobutane, dimethyl ether, carbon dioxide, nitrous oxide, and combinations thereof.

Ingredient s) is a solvent. The amount of ingredient s) in the topical composition is typically about 0 to about 95%. Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols.

Ingredient t) is a humectant. The amount of ingredient t) in the topical composition is typically 0 to 95%. Suitable humectants include glycerin, sorbitol, sodium 2-pyrrolidone-5-carboxylate, soluble collagen, dibutyl phthalate, gelatin, and combinations thereof. Specific humectants include glycerin.

Ingredient u) is a thickener. The amount of ingredient u) in the topical com-position is typically about 0 to about 95%.

Ingredient v) is a powder. The amount of ingredient v) in the topical composition is typically 0 to 95%. Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. For ocular applications, specific powders include beta-cyclodextrin, hydroxypropyl cyclodextrin, and sodium polyacrylate. For gel dosing ocular formulations, sodium polyacrylate may be used.

Ingredient w) is a fragrance. The amount of ingredient w) in the topical composition is typically about 0 to about 0.5%, particularly, about 0.001 to about 0.1%. For ocular applications a fragrance is not generally used.

Ingredient x) is a pigment. Suitable pigments for skin applications include inorganic pigments, organic lake pigments, pearlescent pigments, and mixtures thereof. Inorganic pigments useful in this invention include those selected from the group consisting of rutile or anatase titanium dioxide, coded in the Color Index under the reference CI 77,891; black, yellow, red and brown iron oxides, coded under references CI 77,499, 77,492 and, 77,491; manganese violet (CI 77,742); ultramarine blue (CI 77,007); chromium oxide (CI 77,288); chromium hydrate (CI 77,289); and ferric blue (CI 77,510) and mixtures thereof.

The organic pigments and lakes useful in this invention include those selected from the group consisting of D&C Red No. 19 (CI 45,170), D&C Red No. 9 (CI 15,585), D&C Red No. 21 (CI 45,380), D&C Orange No. 4 (CI 15,510), D&C Orange No. 5 (CI 45,370), D&C Red No. 27 (CI 45,410), D&C Red No. 13 (CI 15,630), D&C Red No. 7 (CI 15,850), D&C Red No. 6 (CI 15,850), D&C Yellow No. 5 (CI 19,140), D&C Red No. 36 (CI 12,085), D&C Orange No. 10 (CI 45,425), D&C Yellow No. 6 (CI 15,985), D&C Red No. 30 (CI 73,360), D&C Red No. 3 (CI 45,430), the dye or lakes based on Cochineal Carmine (CI 75,570) and mixtures thereof.

The pearlescent pigments useful in this invention include those selected from the group consisting of the white pearlescent pigments such as mica coated with titanium oxide, bismuth oxychloride, colored pearlescent pigments such as titanium mica with iron oxides, titanium mica with ferric blue, chromium oxide and the like, titanium mica with an organic pigment of the above-mentioned type as well as those based on bismuth oxychloride and mixtures thereof. The amount of pigment in the topical composition is typically about 0 to about 10%. For ocular applications a pigment is not generally used.

In a particularly preferred embodiment of the invention, topical pharmaceutical compositions for ocular administration are prepared typically comprising component A and B (a carrier), such as purified water, and one or more ingredients selected from the group consisting of y) sugars or sugar alcohols such as dextrans, particularly dextran 70, z) cellulose or a derivative thereof, aa) a salt, bb) disodium EDTA (Edetate disodium), and cc) a pH adjusting additive.

Examples of z) cellulose derivatives suitable for use in the topical pharmaceutical composition for ocular administration include sodium carboxymethylcellulose, ethylcellulose, methylcellulose, and hydroxypropyl-methylcellulose, particularly, hydroxypropyl-methylcellulose.

Examples of aa) salts suitable for use in the topical pharmaceutical composition for ocular administration include mono-, di- and trisodium phosphate, sodium chloride, potassium chloride, and combinations thereof.

Examples of cc) pH adjusting additives include HCl or NaOH in amounts sufficient to adjust the pH of the topical pharmaceutical composition for ocular administration to 6.8-7.5.

Component A may be included in kits comprising component A, a systemic or topical composition described above, or both; and information, instructions, or both that use of the kit will provide treatment for cosmetic and medical conditions in mammals (particularly humans). The information and instructions may be in the form of words, pictures, or both, and the like. In addition or in the alternative, the kit may comprise the medicament, a composition, or both; and information, instructions, or both, regarding methods of application of medicament, or of composition, preferably with the benefit of treating or preventing cosmetic and medical conditions in mammals (e.g., humans).

The invention will be further explained by the following illustrative examples that are intended to be non-limiting.

Procedures for preparation of the isoquinolines are described in the following examples.

All temperatures are given in degrees Centigrade. Reagents were purchased from commercial sources or prepared following literature procedures.

Unless otherwise noted, HPLC purification was performed by redissolving the residue in a small volume of DMSO and filtering through a 0.45 micron (nylon disc) syringe filter. The solution was then purified using a 50 mm Varian Dynamax HPLC 21.4 mm Microsorb Guard-8 $C_8$ column. The initial concentration of 40-80% MeOH:$H_2O$ was selected as appropriate for the target compound. This initial gradient was maintained for 0.5 minutes then increased to 100% MeOH:0% $H_2O$ over 5 minutes. 100% MeOH was maintained for 2 more minutes before it was re-equilibrated back to the initial starting gradient. Total run time was 8 minutes. The resulting fractions were analyzed, combined as appropriate, and then evaporated to provide purified material.

Proton magnetic resonance ($^1$H NMR) spectra were recorded on either a Varian INOVA 400 MHz ($^1$H) NMR spectrometer, Varian INOVA 500 MHz ($^1$H) NMR spectrometer, Bruker ARX 300 MHz ($^1$H) NMR spectrometer, Bruker DPX 400 MHz ($^1$H) NMR spectrometer, or a Bruker DRX 500 MHz ($^1$H) NMR spectrometer. All spectra were determined in the solvents indicated. Although chemical shifts are reported in ppm downfield of tetramethylsilane, they are referenced to the residual proton peak of the respective solvent peak for $^1$H NMR. Interproton coupling constants are reported in Hertz (Hz). Analytical HPLC was performed using a Phenomenex Aqua 5 micron $C_{18}$ 125 Å 50×4.60 mm column coupled with an Agilent 1100 series VWD UV detector. A neutral 0.1% BES (w/v) pH 7.1 buffer with LiOH and 1% $CH_3CN$ in $H_2O$ is used as the aqueous phase. The initial gradient was 55% MeOH aqueous buffer which was increased to 100% MeOH over 3 minutes. 100% MeOH was maintained for 2 minutes before it was re-equilibrated to the initial starting gradient. Spectra were analyzed at 254 nm. LCMS spectra were obtained using a Thermofinnigan AQA MS ESI instrument. The samples were passed through a Phenomenex Aqua 5 micron $C_{18}$ 125 Å 50×4.60 mm column. The initial gradient was 55% MeOH: 1% $CH_3CN$ in $H_2O$ which was increased to 100% MeOH over 3 minutes. 100% MeOH was maintained for 2 minutes before it was re-equilibrated to the initial starting gradient. The spray setting for the MS probe was at 350 μL/min with a cone voltage at 25 mV and a probe temperature at 450 °C.

The following preparations illustrate procedures for the preparation of intermediates and methods for the preparation of isoquinolines.

General Procedure for the Synthesis of Isoquinolines According to Scheme 2

Step 1: Synthesis of 2-Chloro-N-isoquinolin-6-yl-acetamide: A 2.0-mL vial equipped with a stirrer bar was charged with 6-aminoisoquinoline (100 mg, 0.7 mmol) in THF (1.0 mL) and cooled to −78° C. Lithium diisopropylamine (40 μL, 0.35 mmol) was added to the reaction at −78° C. followed by dropwise addition of chloroacetylchloride (62 μL, 0.7 mmol). The reaction was allowed to warm to room temperature and stirred for 30 min. The reaction was concentrated in vacuo then the solid was triturated with cold methanol. The solid was collected by filtration to afford 2-chloro-N-isoquinolin-6-yl-acetamide (58 mg, 38%). $^1$H NMR (400 MHz, DMSO-$d_6$) δ ppm 3.14 (s, 2H) 8.01 (dd, J=9.08, 1.66 Hz, 1H) 8.45 (d, J=8.98 Hz, 2H) 8.66 (d, J=1.56 Hz, 1H) 11.46 (s, 1H); LCMS: 221 (M+H).

Step 2: Synthesis of Isoquinolines: A 1.0 mL vial equipped with a stirrer bar was charged with 2-chloro-N-isoquinolin-6-yl-acetamide (See Step 1, 30 mg, 0.14 mmol), DMF (1.0 mL), potassium iodide (70 mg, 0.42 mmol) and stirred at 45° C. for 30 min. The corresponding substituted aniline (0.42 mmol) was added and stirred for 2 h. Upon completion the reaction was concentrated in vacuo and the residue was purified by prep-HPLC to afford the final isoquinoline.

EXAMPLE 1

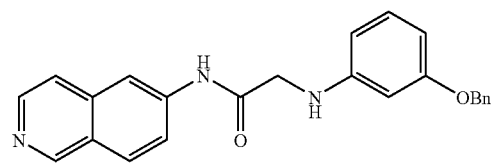

2-(3-Benzyloxy-phenylamino)-N-isoquinolin-6-yl-acetamide: The title compound was obtained as described in Step 2: $^1$H NMR (400 MHz, METHANOL-$d_4$) δ ppm 3.93-3.97 (m, 2H) 4.99-5.02 (m, 2H) 6.27-6.33 (m, 2H) 6.33-6.39 (m, 1H) 7.04 (t, J=8.09 Hz, 1H) 7.16-7.41 (m, 6H) 7.68-7.76 (m, 2H) 8.02 (d, J=8.89 Hz, 1H) 8.31-8.37 (m, 2H) 9.09 (s, 1H); LCMS: 384 (M+H).

EXAMPLE 2

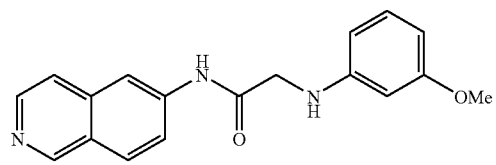

N-Isoquinolin-6-yl-2-(3-methoxy-phenylamino)-acetamide: The title compound was obtained as described in Step 2: $^1$H NMR (400 MHz, METHANOL-$d_4$) δ ppm 3.71 (s, 3H) 3.95 (s, 2H) 6.21-6.33 (m, 2H) 7.04 (t, J=8.00 Hz, 1H) 7.66-7.76 (m, 2H) 8.01 (d, J=8.98 Hz, 1H) 8.29-8.37 (m, 2H) 9.08 (s, 1H); LCMS: 308 (M+H).

EXAMPLE 3

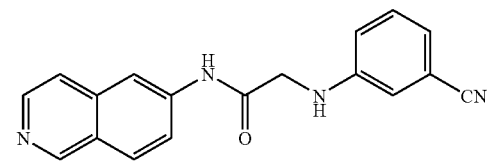

2-(3-Cyano-phenylamino)-N-isoquinolin-6-yl-acetamide: The title compound was obtained as described in Step 2: $^1$H NMR (400 MHz, METHANOL-$d_4$) δ ppm 4.04 (s, 2H) 6.92-7.02 (m, 3H) 7.25-7.34 (m, 1H) 7.75 (dd, J=8.88, 2.05 Hz, 2H) 8.05 (d, J=8.98 Hz, 1H) 8.36 (d, J=1.95 Hz, 2H) 9.10 (s, 1H); LCMS: 303 (M+H).

EXAMPLE 4

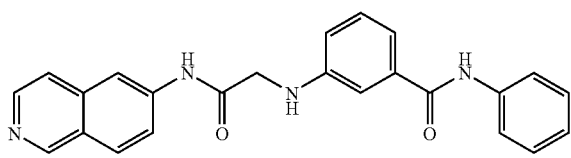

3-[(Isoquinolin-6-ylcarbamoylmethyl)-amino]-N-phenyl-benzamide: The title compound was obtained as described in Step 2: $^1$H NMR (400 MHz, METHANOL-$d_4$) δ ppm 4.07 (s, 2H) 7.09-7.14 (m, 1H) 7.22-7.25 (m, 2H) 7.27-7.36 (m, 4H) 7.61-7.66 (m, 2H) 7.71 (d, J=5.86 Hz, 1H) 7.75 (dd, J=8.88, 2.05 Hz, 1H) 8.03 (d, J=8.98 Hz, 1H) 8.32-8.35 (m, 1H) 8.36 (d, J=1.95 Hz, 1H) 9.09 (s, 1H); LCMS: 397 (M+H).

EXAMPLE 5

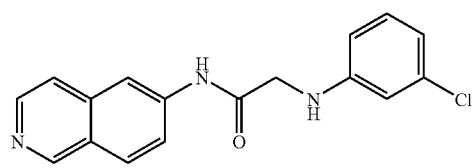

2-(3-Chloro-phenylamino)-N-isoquinolin-6-yl-acetamide: The title compound was obtained as described in Step 2: $^1$H NMR (400 MHz, METHANOL-$d_4$) δ ppm 3.99 (s, 2H) 6.56-6.60 (m, 1H) 6.63-6.69 (m, 2H) 7.09 (t, J=8.00 Hz, 1H) 7.70-7.77 (m, 2H) 8.04 (d, J=8.98 Hz, 1H) 8.32-8.37 (m, 2H) 9.09 (s, 1H); LCMS: 312 (M+H).

EXAMPLE 6

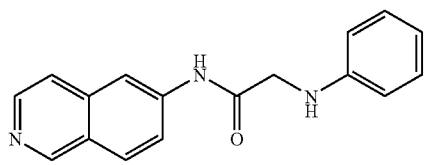

N-Isoquinolin-6-yl-2-phenylamino-acetamide: The title compound was obtained as described in Step 2: $^1$H NMR (400 MHz, METHANOL-$d_4$) δ ppm 3.97 (s, 2H) 6.65-6.75 (m, 3H) 7.10-7.19 (m, 2H) 7.67-7.78 (m, 2H) 8.02 (d, J=8.98 Hz, 1H) 8.30-8.38 (m, 2H) 9.09 (s, 1H); LCMS: 278 (M+H).

EXAMPLE 7

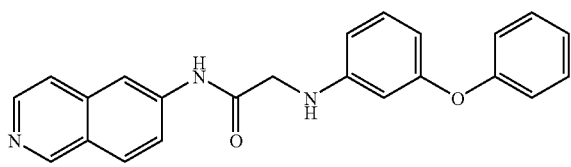

N-Isoquinolin-6-yl-2-(3-phenoxy-phenylaramino)-acetamide: The title compound was obtained as described in Step 2: $^1$H NMR (400 MHz, METHANOL-$d_4$) δ ppm 3.93-3.95 (m, 2H) 6.28-6.33 (m, 2H) 6.42-6.48 (m, 1H) 6.91-6.96 (m, 2H) 6.99 (t, J=7.32 Hz, 1H) 7.08-7.15 (m, 1H) 7.19-7.25 (m, 2H) 7.69-7.74 (m, 2H) 8.03 (d, J=8.79 Hz, 1H) 8.31-8.38 (m, 2H) 9.10 (s, 1H); LCMS: 370 (M+H).

EXAMPLE 8

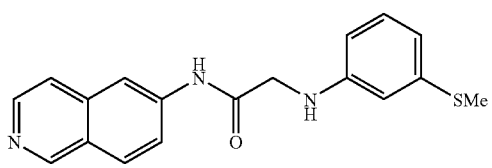

N-Isoquinolin-6-yl-2-(3-methylsulfanyl-phenylamino)-acetamide: The title compound was obtained as described in Step 2: $^1$H NMR (400 MHz, METHANOL-$d_4$) δ ppm 2.40 (s, 3H) 3.97 (s, 2H) 6.43-6.48 (m, 1H) 6.58-6.62 (m, 2H) 7.03-7.10 (m, 1H) 7.68-7.76 (m, 2H) 8.02 (d, J=8.98 Hz, 1H) 8.31-8.36 (m, 2H) 9.08 (s, 1H); LCMS: 324 (M+H).

EXAMPLE 9

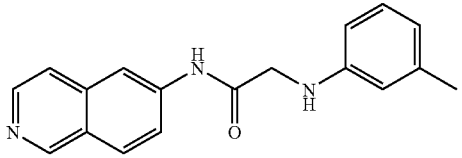

N-Isoquinolin-6-yl-2-m-tolylamino-acetamide: The title compound was obtained as described in Step 2: $^1$H NMR (400 MHz, METHANOL-$d_4$) δ ppm 2.23 (s, 3H) 3.95 (s, 2H) 6.43-6.57 (m, 3H) 7.02 (t, J=7.71 Hz, 1H) 7.67-7.77 (m, 2H) 8.02 (d, J=8.98 Hz, 1H) 8.30-8.37 (m, 2H) 9.08 (s, 1H); LCMS: 292 (M+H).

EXAMPLE 10

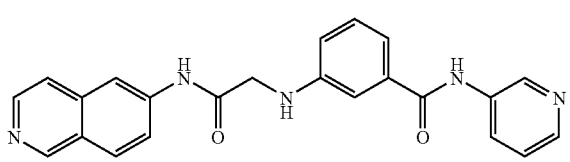

3-[(Isoquinolin-6-ylcarbamoylmethyl)-amino]-N-pyridin-3-yl-benzamide: The title compound was obtained as described in Step 2: $^1$H NMR (400 MHz, METHANOL-$d_4$) δ ppm 4.08 (s, 2H) 6.89-6.94 (m, 1H) 7.24-7.33 (m, 3H) 7.42 (dd, J=8.40, 4.88 Hz, 1H) 7.71 (d, J=5.86 Hz, 1H) 7.75 (dd, J=8.88, 2.05 Hz, 1H) 8.03 (d, J=8.98 Hz, 1H) 8.19-8.24 (m, 1H) 8.28 (dd, J=4.78, 1.46 Hz, 1H) 8.33 (d, J=5.86 Hz, 1H) 8.36 (d, J=1.76 Hz, 1H) 8.85 (d, J=2.54 Hz, 1H) 9.09 (s, 1H); LCMS: 398 (M+H).

EXAMPLE 11

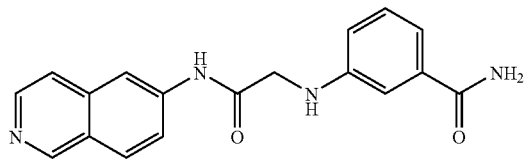

3-[(Isoquinolin-6-ylcarbamoylmethyl)-amino]-benzamide: The title compound was obtained as described in Step 2: ¹H NMR (400 MHz, METHANOL-d$_4$) δ ppm 4.04 (s, 2H) 6.84-6.88 (m, 1H) 7.15-7.20 (m, 2H) 7.24 (t, J=7.91 Hz, 1H) 7.71 (d, J=5.86 Hz, 1H) 7.74 (dd, J=8.98, 2.15 Hz, 1H) 8.02 (d, J=8.98 Hz, 1H) 8.36 (t, J=2.44 Hz, 2H) 9.09 (s, 1H); LCMS: 321 (M+H).

EXAMPLE 12

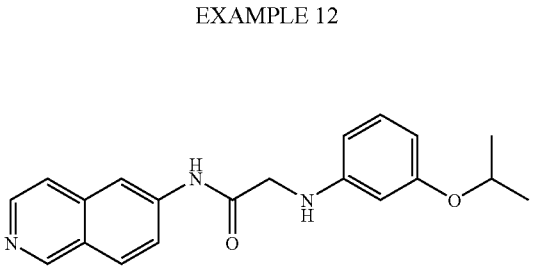

2-(3-Isopropoxy-phenylamino)-N-isoquinolin-6-yl-acetamide: The title compound was obtained as described in Step 2: ¹H NMR (400 MHz, METHANOL-d$_4$) δ ppm 1.24 (d, J=6.05 Hz, 6H) 3.95 (s, 2H) 4.45-4.55 (m, 1H) 6.23 (t, J=2.25 Hz, 1H) 6.25-6.30 (m, 2H) 7.03 (t, J=8.10 Hz, 1H) 7.69-7.76 (m, 2H) 8.02 (d, J=8.79 Hz, 1H) 8.32-8.36 (m, 2H) 9.09 (s, 1H); LCMS: 336 (M+H).

EXAMPLE 13

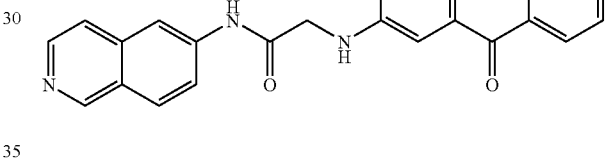

N-Isoquinolin-6-yl-2-(3-sulfamoyl-phenylamino)-acetamide: The title compound was obtained as described in Step 2: ¹H NMR (400 MHz, METHANOL-d$_4$) δ ppm 4.05 (s, 2H) 6.85-6.89 (m, 1H) 7.18-7.22 (m, 2H) 7.30 (t, J=8.20 Hz, 1H) 7.70 (d, J=5.86 Hz, 1H) 7.74 (dd, J=8.88, 2.05 Hz, 1H) 8.03 (d, J=8.98 Hz, 1H) 8.32-8.36 (m, 2H) 9.09 (s, 1H); LCMS: 357 (M+H).

EXAMPLE 14

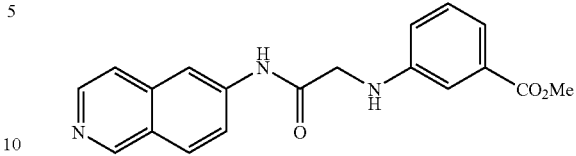

3-[(Isoquinolin-6-ylcarbamoylmethyl)-amino]-benzoic acid methyl ester: The title compound was obtained as described in Step 2: ¹H NMR (400 MHz, METHANOL-d$_4$) δ ppm 3.84 (s, 3H) 4.04 (s, 2H) 6.89-6.94 (m, 1H) 7.25 (t, J=7.81 Hz, 1H) 7.31-7.36 (m, 2H) 7.74-7.79 (m, 2H) 8.06 (d, J=8.98 Hz, 1H) 8.34 (d, J=6.05 Hz, 1H) 8.38 (d, J=1.95 Hz, 1H) 9.12 (s, 1H); LCMS: 336 (M+H).

EXAMPLE 15

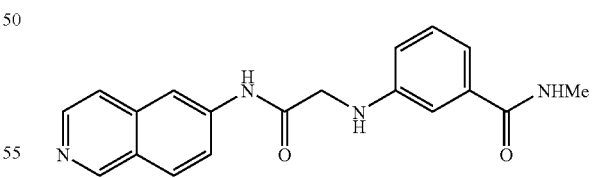

2-(3-Benzoyl-phenylamino)-N-isoquinolin-6-yl-acetamide: The title compound was obtained as described in Step 2: ¹H NMR (400 MHz, METHANOL-d$_4$) δ ppm 4.02 (s, 2H) 6.95-7.00 (m, 1H) 7.02-7.04 (m, 1H) 7.05-7.09 (m, 1H) 7.30 (t, J=7.81 Hz, 1H) 7.35-7.41 (m, 2H) 7.48-7.55 (m, 1H) 7.69-7.76 (m, 4H) 8.04 (d, J=8.98 Hz, 1H) 8.33-8.37 (m, 2H) 9.10 (s, 1H); LCMS: 382 (M+H).

EXAMPLE 16

3-[(Isoquinolin-6-ylcarbamoylmethyl)-amino]-N-methyl-benzamide: The title compound was obtained as described in Step 2: ¹H NMR (400 MHz, METHANOL-d$_4$) δ ppm 2.87 (s, 3H) 4.04 (s, 2H) 6.83 (dd, J=8.20, 2.54 Hz, 1H) 7.06-7.11 (m, 1H) 7.11-7.14 (m, 1H) 7.22 (t, J=7.81 Hz, 1H) 7.70 (d, J=5.86 Hz, 1H) 7.74 (dd, J=8.88, 2.05 Hz, 1H) 8.02 (d, J=8.98 Hz, 1H) 8.30-8.37 (m, 2H) 9.08 (s, 1H); LCMS: 335 (M+H).

EXAMPLE 17

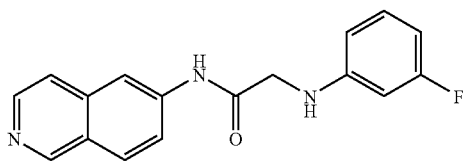

2-(3-Fluoro-phenylamino)-N-isoquinolin-6-yl-acetamide: The title compound was obtained as described in Step 2: $^1$H NMR (400 MHz, METHANOL-$d_4$) δ ppm 3.98 (s, 2H) 6.34-6.41 (m, 2H) 6.45-6.49 (m, 1H) 7.07-7.14 (m, 1H) 7.71 (d, J=5.86 Hz, 1H) 7.73 (dd, J=8.88, 2.05 Hz, 1H) 8.03 (d, J=8.79 Hz, 1H) 8.31-8.38 (m, 2H) 9.09 (s, 1H); LCMS: 296 (M+H).

EXAMPLE 18

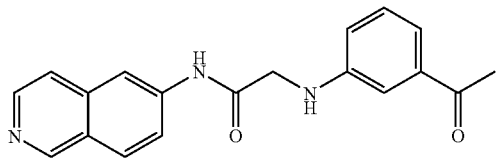

2-(3-Acetyl-phenylamino)-N-isoquinolin-6-yl-acetamide: The title compound was obtained as described in Step 2: $^1$H NMR (400 MHz, METHANOL-$d_4$) δ ppm 2.54 (s, 3H) 4.05 (s, 2H) 6.91-6.95 (m, 1H) 7.25-7.30 (m, 2H) 7.31-7.35 (m, 1H) 7.71 (d, J=5.86 Hz, 1H) 7.74 (dd, J=8.88, 2.05 Hz, 1H) 8.03 (d, J=8.79 Hz, 1H) 8.31-8.37 (m, 2H) 9.09 (s, 1H); LCMS: 320 (M+H).

Reference Example One:

The inhibition of G-protein-coupled receptor kinases including hGRK-2 was determined for isoquinoline compounds as disclosed herein using a biochemical assay. The inhibition of GRK-3, GRK-5 and GRK-6 was also determined using the same assay.

The protein kinase inhibition was determined using a biochemical assay utilizing the light emission of a luciferase reaction. The luciferase-based assay operates on the following reaction principles:

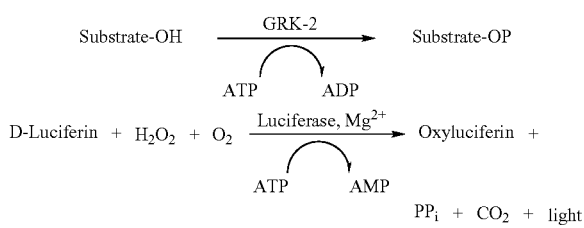

An inhibitor of GRK-2 will increase the amount of ATP in solution as shown. Thus, an inhibitor of GRK-2 will drive the luciferase reaction to the right, resulting in more light emitted. The amount of light emitted is proportional to the inhibition resulting from the GRK-2 inhibitor. The luciferase assay was also used to test the inhibition properties of other kinases. The results of the assay for GRK-2, GRK-3, GRK-5, and GRK-6 are presented below in Table 1.

The test procedure was as follows:

Assay Buffer:
50 mM HEPES, pH 7.5
10 mM $MgCl_2$
100 μM activated sodium orthovanadate
0.01% CHAPS
0.1% BSA
1 mM DTT (added fresh daily)

10× Assay Buffer Stock:
500 mM HEPES, pH 7.5
100 mM $MgCl_2$
1 mM activated sodium orthovanadate
0.1% CHAPS
1% BSA (leave out for 10× compound dilution buffer)

Final Assay Conditions:
50 μM test compound
20 μM casein
10 μM ATP
50 nM hGRK2
4.5% DMSO
90-120 minute incubation Stopped by addition of 30 μl 3×-diluted Kinase-Glo reagent containing 0.01% trypan blue. Counted on FUSION plate reader.

Protocol

Compound Dilution and Transfer

Prepare sufficient buffer containing 40% DMSO to add 20 μl/well to the number of plates being assayed. This buffer should not contain BSA because it will precipitate with addition of 40% DMSO. (EXAMPLE: To make 3000 ml compound dilution buffer: 1200 ml DMSO, 180 ml 10× compound dilution buffer, 1615 ml ultrapure water, 3 ml 1 M DTT.).

Using Multidrop, add 20 μl of compound dilution buffer to all wells of the 384-well daughter plate (add 1 μl DMSO to control wells). This will result in a daughter plate which contains 21 μl of ~500 μM test compound.

Using the PlateTrak, transfer 5 μl of the test compounds to a 384-well, non-binding, white microtiter plate (Costar XXXX).

GRK2/ATP Addition

Prepare sufficient volume of buffer (with BSA and 1 mM DTT) containing 125 nM GRK2 and 25 μM ATP. (EXAMPLE: To 219 ml buffer add 550 μl 10 mM ATP and 350 μl 79 μM GRK2).

Using Multidrop, add 20 μl of GRK2/ATP mixture to all wells of the microtiter plate.

Casein Addition

Prepare sufficient volume of buffer (with BSA and 1 mM DTT) containing 40 μM casein. (EXAMPLE: To 211 ml buffer add 8.8 ml 1 mM casein)

Using Multidrop, add 25 μl to columns 1 through 23 of the microtiter plate. Add 25 μl of complete buffer to column 24 (blanks).

Incubation

Mix reaction gently by tapping (Multidrop addition of casein does a decent job of mixing), stack plates and incubate at room temperature for between 90 and 120 minutes. Assay progression can be tracked in a separate plate if desired.

Target 20-30% ATP consumption. Try to avoid exceeding 40% consumption as kinetics might become non-linear due to substrate (ATP) depletion.

Addition of Kinase-glo Reagents

The Kinase-Glo reagent can be diluted 3-fold with no loss of data quality in this assay. Additionally, since the library contains many colored compounds which will quench the light emitted from the well resulting in a false negative (kinase inhibitors result in less ATP consumption thus more light emitted), the entire reaction is subject to intentional quench to override this effect. This intentional quench is accomplished by the addition of 0.01% trypan blue to the Kinase-Glo reagents. (EXAMPLE: 100 ml 1× Kinase-Glo reagents (prepared according to product insert), 200 ml assay buffer, 7.5 ml 0.4% trypan blue.

Using Multidrop, add 30 µl to all wells of the assay plate.

Count on FUSION plate reader in luminescence mode.

The inhibition results for the foregoing Examples 1-18 are for quinolines having the following general isoquinoline structure:

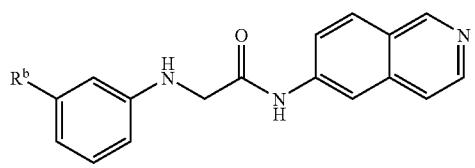

wherein $R^b$ is given separately for each example below in Table 1. The results are provided in terms of Ki (nM):

10-100 nM Ki—++++
100-1000 nM Ki—+++
1000-10,000 nM Ki—++
>10,000 nM Ki—+.

TABLE 1

| EX. | $R^b$ | GRK-2 | Max. Inhib. (%) (GRK2) | GRK-3 | GRK-5 | GRK-6 |
|---|---|---|---|---|---|---|
| 1 | OBn | +++ | 112 | +++ | +++ | + |
| 2 | OMe | ++++ | 103 | ++++ | +++ | +++ |
| 3 | CN | ++ | 91 | ++ | − | + |
| 4 | CONHPh | ++++ | 99 | ++++ | +++ | ++ |
| 5 | Cl | +++ | 102 | +++ | ++ | ++ |
| 6 | H | +++ | 112 | +++ | ++ | ++ |
| 7 | OPh | +++ | 104 | +++ | ++ | ++ |
| 8 | SMe | ++++ | 108 | ++++ | ++ | ++ |
| 9 | Me | +++ | 100 | +++ | ++ | ++ |
| 10 | CONH-m-Pyridine | ++++ | 106 | ++++ | +++ | +++ |
| 11 | $CONH_2$ | ++++ | 102 | ++++ | ++ | ++ |
| 12 | O-iPr | ++++ | 118 | ++++ | ++ | + |
| 13 | $SO_2NH_2$ | ++ | 115 | ++ | + | + |
| 14 | COOMe | +++ | 104 | +++ | + | + |
| 15 | COPh | ++ | 119 | ++ | + | + |
| 16 | CONHMe | ++++ | 113 | ++++ | ++ | ++ |
| 17 | F | +++ | 120 | ++++ | ++ | ++ |
| 18 | COMe | +++ | 116 | +++ | + | + |

EXAMPLE 19

An isoquinoline having the following structure was prepared as described above according to scheme 2.

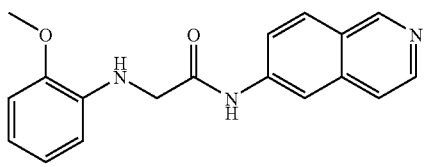

N-Isoquinolin-6-yl-2-(2-methoxy-phenylamino)-acetamide: The title compound was obtained as described in Step 2: $^1$H NMR (400 MHz, METHANOL-$d_4$) δ ppm 3.89 (s, 3H) 4.00 (s, 2H) 6.54 (dd, J=7.81, 1.56 Hz, 1H) 6.67-6.72 (m, J=7.61, 1.56 Hz, 1H) 6.78-6.83 (m, J=7.71, 1.46 Hz, 1H) 6.87 (dd, J=7.91, 1.27 Hz, 1H) 7.68-7.77 (m, 2H) 8.03 (d, J=8.98 Hz, 1H) 8.32-8.38 (m, 2H) 9.09 (s, 1H); LCMS: 308 (M+H).

This isoquinoline was also tested using the luciferase biochemical assay. The maximum inhibition was 109% for GRK-2. The results in $K_i$ (nM) using the scale above were as follows:

GRK-2—++
GRK-3—++
GRK-5—+
GRK-6—++

EXAMPLE 20

An isoquinoline having the following structure was prepared as described above according to scheme 2.

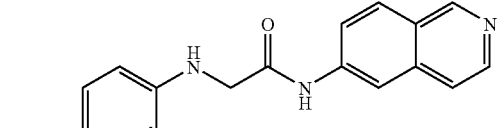

N-Isoquinolin-6-yl-2-(4-methoxy-phenylamino)-acetamide: The title compound was obtained as described in Step 2: $^1$H NMR (400 MHz, METHANOL-$d_4$) δ ppm 3.69 (s, 3H) 3.91 (s, 2H) 6.61-6.69 (m, 2H) 6.74-6.82 (m, 2H) 7.67-7.79 (m, 2H) 8.03 (d, J=8.79 Hz, 1H) 8.30-8.38 (m, 2H) 9.09 (s, 1H); LCMS: 308 (M+H).

This isoquinoline was also tested using the luciferase biochemical assay. The maximum inhibition was 116% for GRK-2. The results in $K_i$ (nM) using the scale above were as follows:

GRK-2—++
GRK-3—++
GRK-5—+
GRK-6—++

EXAMPLE 21

An isoquinoline having the following structure was prepared as described above according to scheme 2.

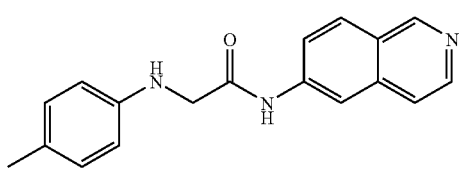

N-Isoquinolin-6-yl-2-p-tolylamino-acetamide: The title compound was obtained as described in Step 2: $^1$H NMR (400 MHz, METHANOL-$d_4$) δ ppm 2.19 (s, 3H) 3.93 (s, 2H) 6.56-6.63 (m, 2H) 6.97 (d, J=8.00 Hz, 2H) 7.66-7.76 (m, 2H) 8.01 (d, J=8.79 Hz, 1H) 8.28-8.37 (m, 2H) 9.08 (s, 1H); LCMS: 292 (M+H).

This isoquinoline was also tested using the luciferase biochemical assay. The maximum inhibition was 116% for GRK-2. The results in $K_i$ (nM) using the scale above were as follows:
GRK-2—++
GRK-3—++
GRK-5—+
GRK-6—++.

EXAMPLE 22

An isoquinoline having the following structure was prepared as described above according to scheme 2.

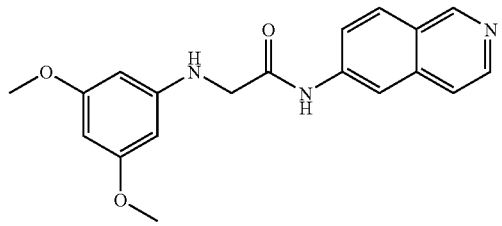

2-(3,5-Dimethoxy-phenylamino)-N-isoquinolin-6-yl-acetamide: The title compound was obtained as described in Step 2: $^1$H NMR (400 MHz, METHANOL-$d_4$) δ ppm 3.70 (s, 6H) 3.94 (s, 2H) 5.82-5.94 (m, 3H) 7.67-7.79 (m, 2H) 8.03 (d, J=8.79 Hz, 1H) 8.28-8.40 (m, 2H) 9.09 (s, 1H); LCMS: 338 (M+H).

This isoquinoline was also tested using the luciferase biochemical assay. The maximum inhibition was 124% for GRK-2. The results in $K_i$ (nM) using the scale above were as follows:
GRK-2—++
GRK-3—++
GRK-5—++
GRK-6—++.

EXAMPLE 23

An isoquinoline having the following structure was prepared as described above according to scheme 2.

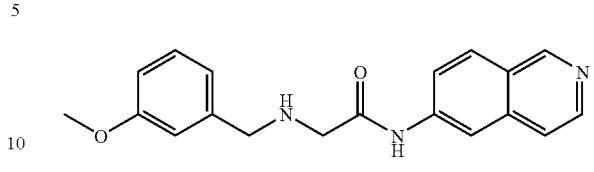

N-Isoquinolin-6-yl-2-(3-methoxy-benzylamino)-acetamide: The title compound was obtained as described in Step 2: $^1$H NMR (400 MHz, METHANOL-$d_4$) δ ppm 3.45 (s, 2H) 3.77 (s, 3H) 3.81 (s, 2H) 6.76-6.83 (m, 1H) 6.91-7.00 (m, 2H) 7.19-7.27 (m, 1H) 7.68-7.76 (m, 2H) 8.04 (d, J=8.79 Hz, 1H) 8.32-8.37 (m, 2H) 9.10 (s, 1H); LCMS: 322 (M+H).

This isoquinoline was also tested using the luciferase biochemical assay. The maximum inhibition was 111% for GRK-2. The results in $K_i$ (nM) using the scale above were as follows:
GRK-2—++
GRK-3—++
GRK-5—+
GRK-6—+.

EXAMPLE 24

An isoquinoline having the following structure was prepared as described above according to scheme 2.

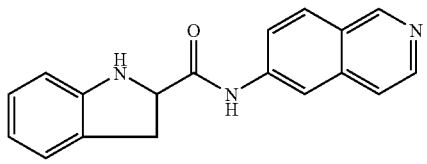

2,3-Dihydro-1H-indole-2-carboxylic acid-isoquinolin-6-yl-amide: To a solution of 6-aminoisoquinoline (25 mg, 0.17 mmol) in DMF (1.0 mL) was added indoline-2-carboxylic acid (30 mg, 0.17 mmol), HATU (70 mg, 0.19 mmol), diisopropylethylamine (35 µL, 0.19 mmol) and stirred overnight at 40° C. The reaction mixture was concentrated and purified by prep-HPLC to afford the titled compound (3.0 mg): $^1$H NMR (400 MHz, METHANOL-$d_4$) δ ppm 3.18 (dd, J=16.11, 8.30 Hz, 1H) 3.56 (dd, J=16.20,10.54 Hz, 1H) 4.52 (dd, J=10.54, 8.40 Hz, 1H) 6.70-6.81 (m, 2H) 6.99-7.10 (m, 3H) 7.73 (d, J=6.05 Hz, 1H) 7.81 (dd, J=8.88, 2.05 Hz, 1H) 8.05 (d, J=8.98 Hz, 1H) 8.35 (d, J=5.86 Hz, 1H) 8.40 (d, J=1.95 Hz, 1H) 9.11 (s, 1H); LCMS: 290 (M+H).

This isoquinoline was also tested using the luciferase biochemical assay. The maximum inhibition was 110% for GRK-2. The results in $K_i$ (nM) using the scale above were as follows:
GRK-2—++
GRK-3—++
GRK-5—+
GRK-6—+.

EXAMPLE 25

The isoquinolines of Examples 2-4 were also screened in cellular assays for GRK-2 inhibitory effect. The results are shown in FIGS. 1-9. The figures show the effect of the three different isoquinolines in the translocation of several receptors. The Transfluor assay (Assay and Drug Development Technologies, Volume 1, Number 1-1, pages 21-30, (2002); U.S. Pat. No. 5,891,646, and U.S. Pat. No. 6,110,693, each incorporated herein by reference in its entirety) was used to measure the degree of translocation in U2OS cells that over express the receptor and arrestin.

Figure 2:
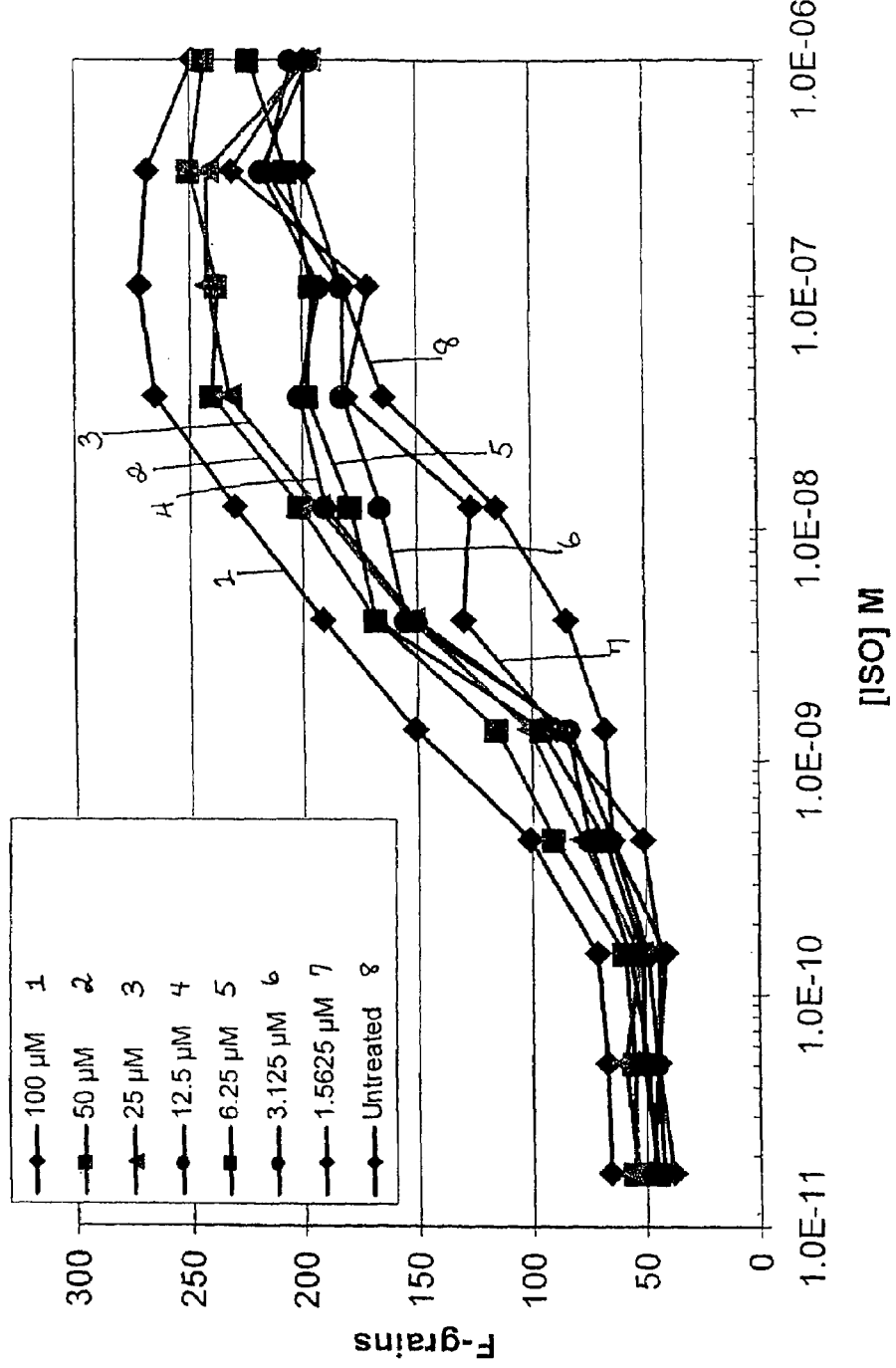
FIG. 2 is a graphical representation of the effect of a 60 minute pre-incubation of the GRK-2 inhibitor of Example 2 on ISO-induced β-arrestin translocation in β1 wt using a Transfluor® assay.
Figure 3:
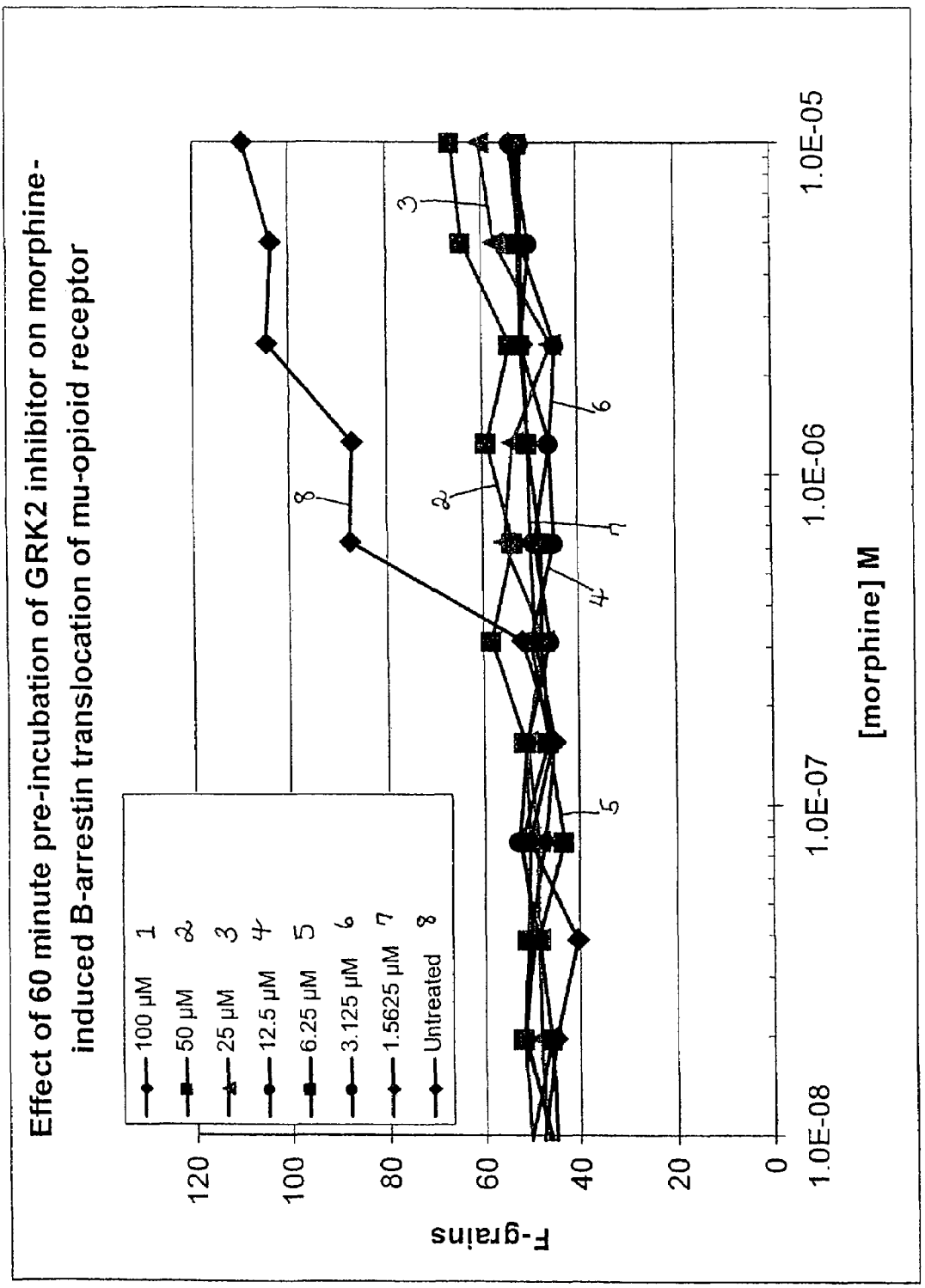
FIG. 3 is a graphical representation of the effect of a 60 minute pre-incubation of the GRK-2 inhibitor of Example 2 on morphine-induced β-arrestin translocation of μ-opioid receptor using a Transfluor® assay.

FIGS. 1-3 show the effect of the isoquinoline described in Example 2 (GRK-2 Ki=0.022 micromolar), in the isoproterenol-induced translocation of arrestin-GFP to the Beta 2 Adrenergic Receptor (B2 wt). FIG. 1 shows dose response curves for the effect of isoproterenol (a Beta 2 Adrenergic receptor agonist) against F-grains (a measure of the degree of arrestin-GFP translocation to the receptor) for increasing concentrations of the isoquinoline (see curves). For any given concentration of isoproterenol, as the concentration of isoquinoline increases, there is a stepwise reduction in translocation (decrease in F-grains). By preventing GRK-2 mediated phosphorylation of the receptor, the isoquinoline prevents binding of arrestin-GFP to the receptor. FIG. 2 shows the same effect on the Beta 1 Adrenergic receptor (B1 wt), and FIG. 2 is the effect on the mu opioid receptor. FIGS. 4-6 and FIGS. 7-9 show the effect of two other isoquinolines, the isoquinoline from Example 3 (GRK-2 Ki=1.8 micromolar) and the isoquinoline of Example 4, (GRK -2 Ki=0.037 micromolar), respectively, in the same three receptors as tested for the isoquinoline of Example 2.

The isoquinoline of Example 2 and the isoquinoline of Example 4, which are very good inhibitors of GRK-2 show modest inhibition of arrestin-GFP translocation to the B2 WT, B1 WT, but strong inhibition to the mu opioid. The isoquinoline of Example 3, however, which is a weaker inhibitor of GRK-2, shows much less inhibition of translocation in all three receptors. Finally, increased concentrations of either the isoquinoline of Example 2 or Example 4 showed increased accumulation of cAMP in HEK-293 cells (Beta 2 Adrenergic receptor overexpressed) in the presence of a fixed concentration of isoproterenol. This is consistent with the inhibition of GRK-2 resulting in less translocation of arrestin-GFP, less desensitization, and consequently more signaling by the B2AR. With more receptors available now on the surface of the cell, more cAMP is being generated in the presence of Isoproterenol. The isoquinoline of Example 3, which is a weak inhibitor of GRK-2 and shows much less inhibition of translocation also has less effect on the amount of cAMP accumulated in the cell.

Figure 4:
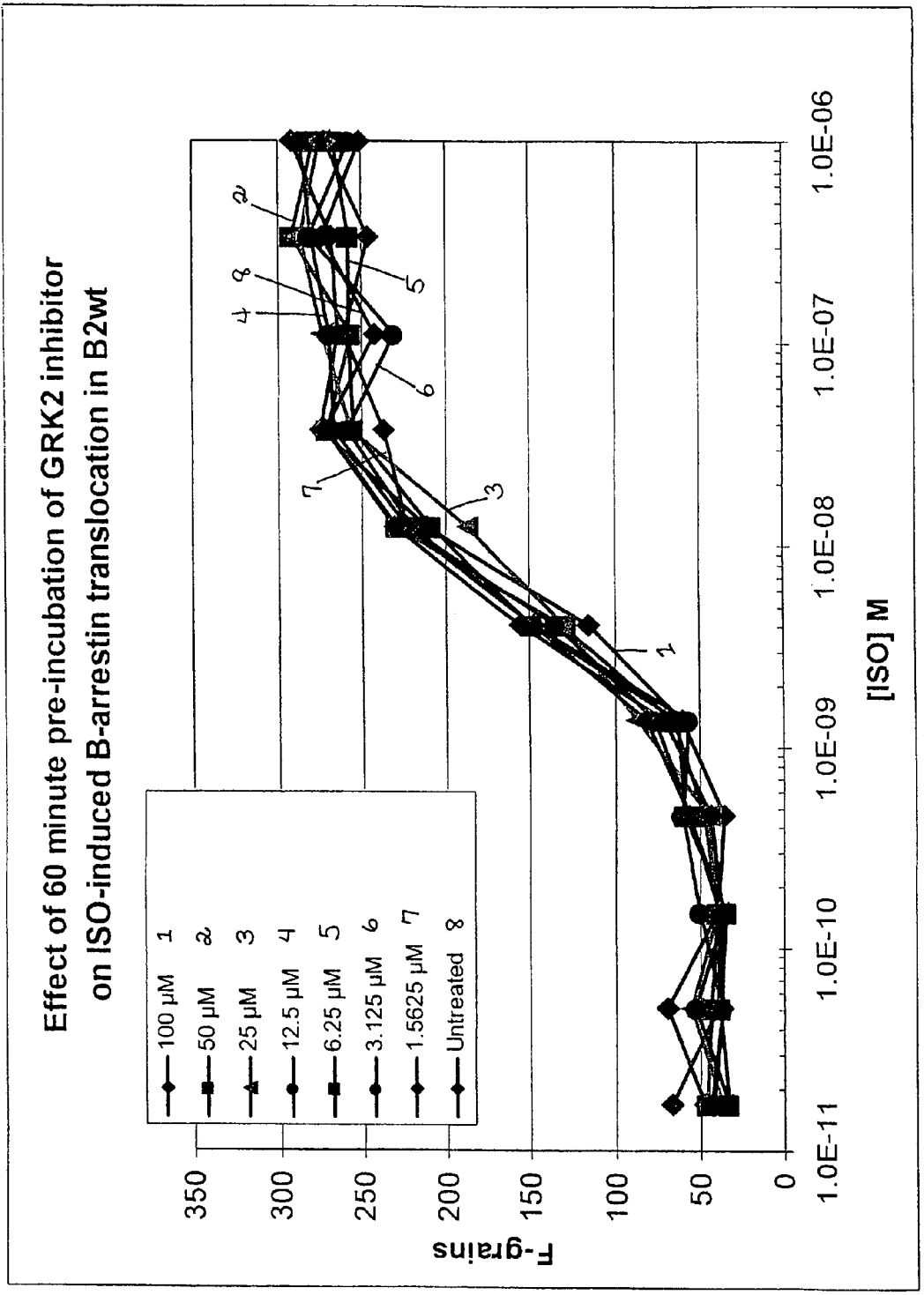
FIG. 4 is a graphical representation of the effect of a 60 minute pre-incubation of the GRK-2 inhibitor of Example 3 on ISO-induced β-arrestin translocation in β2 wt using a Transfluor® assay.
Figure 5:
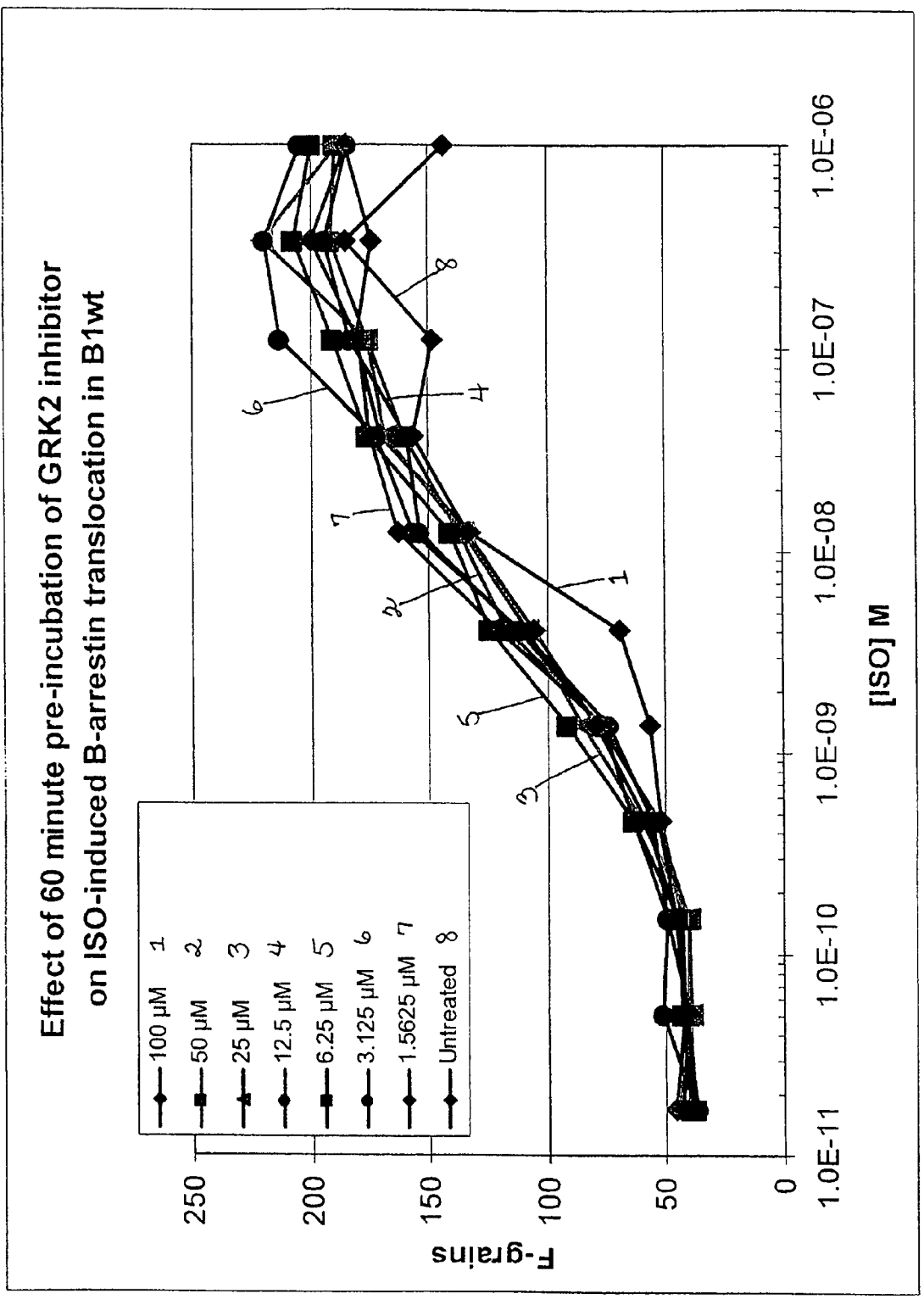
FIG. 5 is a graphical representation of the effect of a 60 minute pre-incubation of the GRK-2 inhibitor of Example 3 on ISO-induced β-arrestin translocation in β1 wt using a Transfluor® assay.
Figure 6:
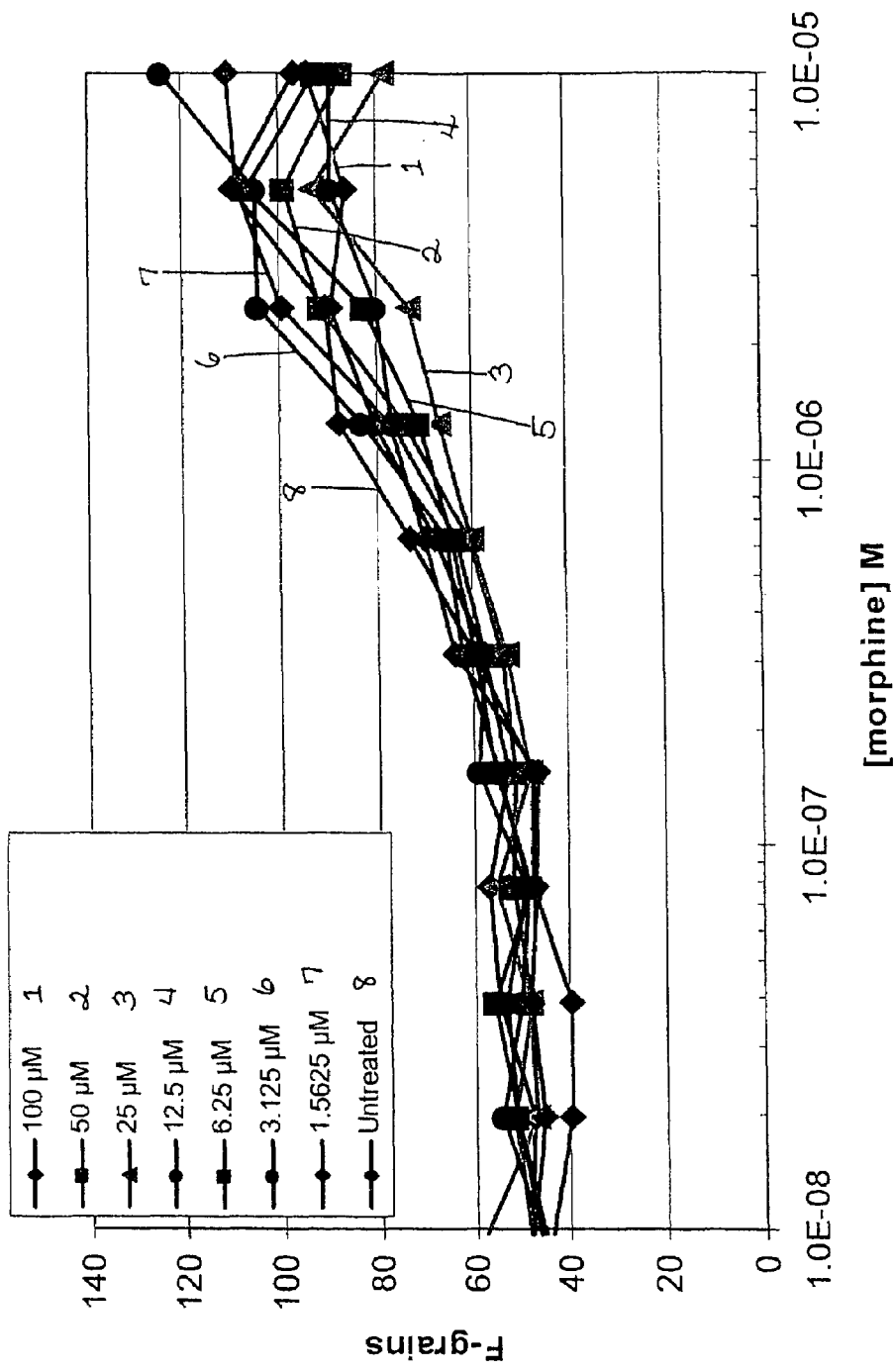
FIG. 6 is a graphical representation of the effect of a 60 minute pre-incubation of the GRK-2 inhibitor of Example 3 on morphine-induced β-arrestin translocation of μ-opioid receptor using a Transfluor® assay.
Figure 7:
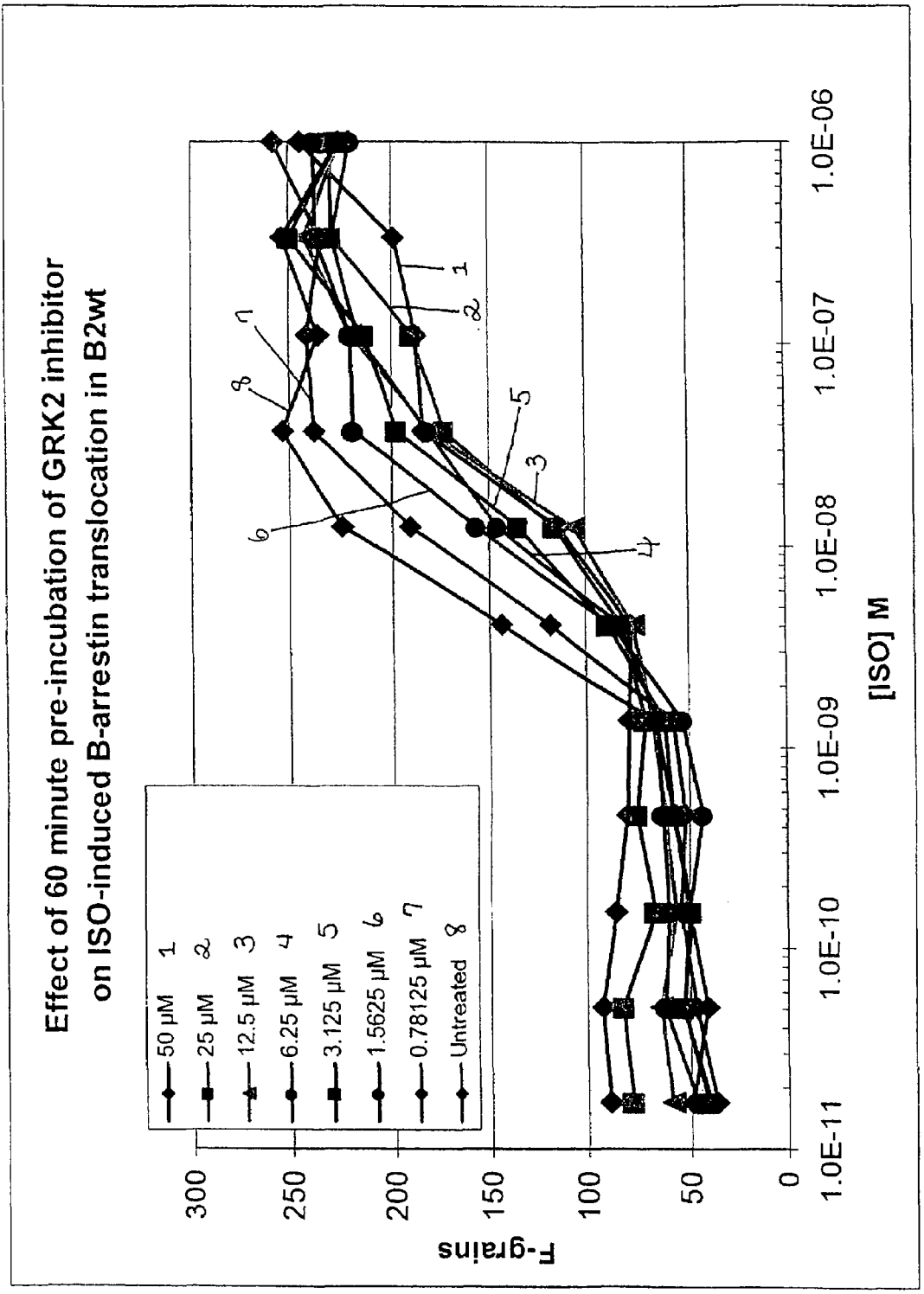
FIG. 7 is a graphical representation of the effect of a 60 minute pre-incubation of the GRK-2 inhibitor of Example 4 on ISO-induced β-arrestin translocation in β2 wt using a Transfluor® assay.
Figure 8:
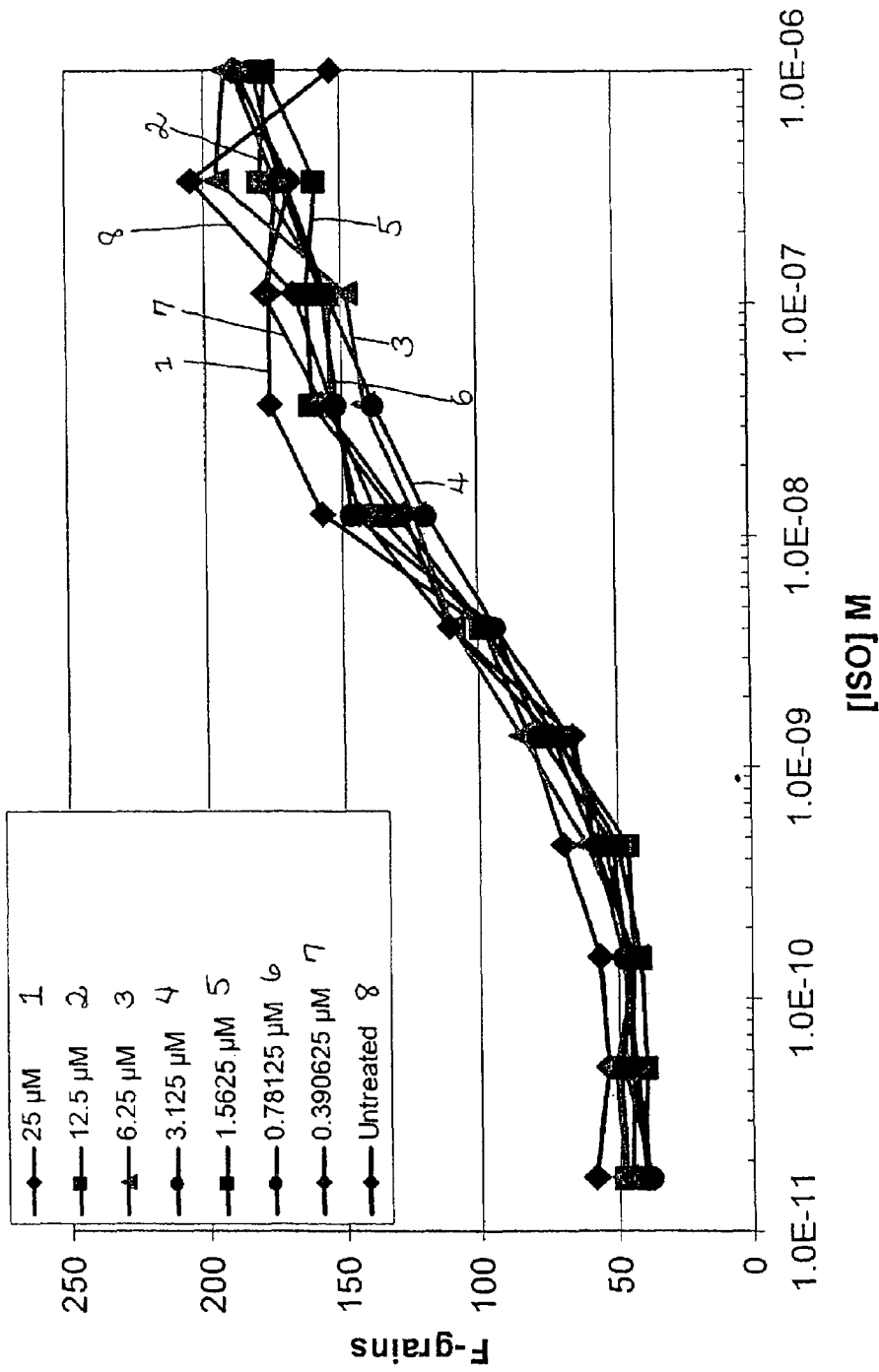
FIG. 8 is a graphical representation of the effect of a 60 minute pre-incubation of the GRK-2 inhibitor of Example 4 on ISO-induced β-arrestin translocation in β1 wt using a Transfluor® assay.
Figure 9:
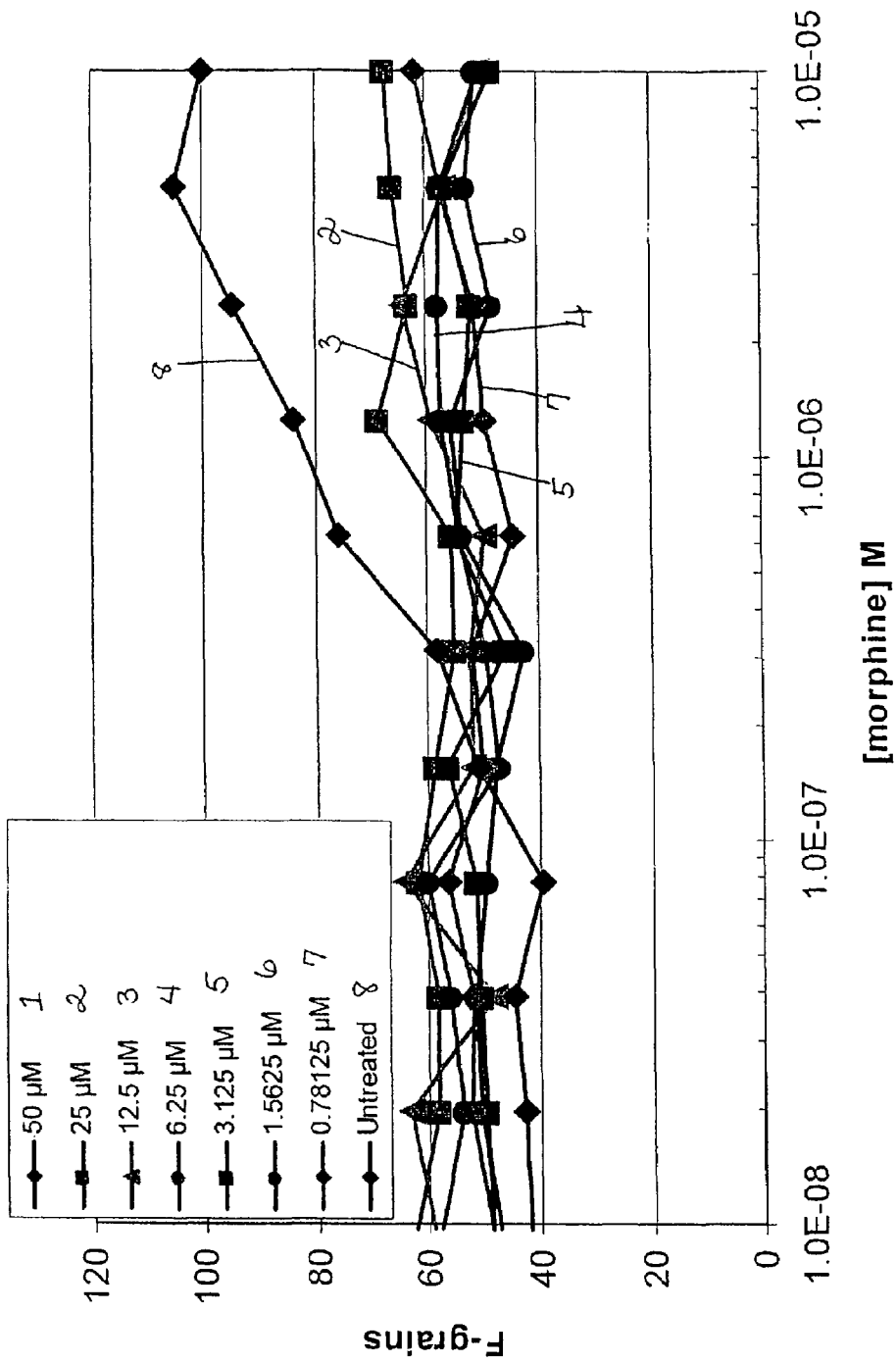
FIG. 9 is a graphical representation of the effect of a 60 minute pre-incubation of the GRK-2 inhibitor of Example 4 on morphine-induced β-arrestin translocation of μ-opioid receptor using a Transfluor® assay.

In FIG. 1, the IC50 of the β2 arrestin was 8 μM. In FIG. 3, the IC50 for the mu-opioid receptor was less than 1 μM. In FIG. 4, the IC50 of the β2 arrestin was greater than 100 μM. In FIG. 5, the IC50 for the β1 arrestin was greater than 100 μM. In FIG. 6, the IC50 for the mu-opioid receptor was greater than 100 μM. In FIG. 7, the IC50 of the β2 arrestin was 4 μM. In FIG. 8, the IC50 for the β1 arrestin was greater than 100 μM. In FIG. 9, the IC50 for the mu-opioid receptor was less than 1 μM.

The isoquinolines may further be screened for effect on GPCR desensitization by use of the methods described in U.S. Patent Application No. 2004/0091946, published May 13, 2004, or U.S. Patent Application No. 2005/0032125, published Feb. 10, 2005, both incorporated herein by reference in their entirety.

EXAMPLE 26

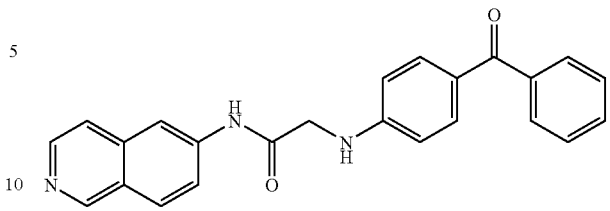

2-(4-Benzoyl-phenylamino)-N-isoquinolin-6-yl-acetamide: The title compound could be obtained as described in Step 2 above.

Reference Example Two:

Cell-based porcine trabecular meshwork (PTM) assay.

The anterior section of porcine eyes was harvested within 4 hours post-mortem. The iris and ciliary body were removed and trabecular meshwork cells were harvested by blunt dissection. Finely minced trabecular meshwork tissue was plated into collagen-coated 6-well plates in Medium-199 containing 20% fetal bovine serum (FBS). After two passages at confluence, cells were transferred to low-glucose DMEM containing 10% FBS. Cells were used between passage 3 and passage 8.

Cells were plated into fibronectin-coated, glass multiwell plates the day before compound testing under standard culture conditions. Compounds were added to cells in the presence of 1% FBS-containing DMEM and 1% DMSO. When compounds were incubated with the cells for the duration determined to be optimal, the media and compound is removed and cells fixed for 20 minutes in 3% methanol-free paraformaldehyde. Cells were rinsed twice with phosphate buffered saline (PBS) and cells are permeabilized with 0.5% Triton X-100 for two minutes. Following an additional two washes with PBS, F-actin was stained with Alexa-fluor 488-labelled phalloidin and nuclei are stained with DAPI.

Data was reduced to the mean straight actin-fiber length and normalized to DMSO-treated control cells (100%) and 50 μM Y-27632 (0%). Y-27632 is a rho-kinase inhibitor known to result in the depolymerization of F-actin in these cells.

EXAMPLE 27

The cellular assay described in Reference Example Two was used to test the foregoing Examples 1-18, the results of which are presented below. For reference, these are isoquinolines having the following general isoquinoline structure:

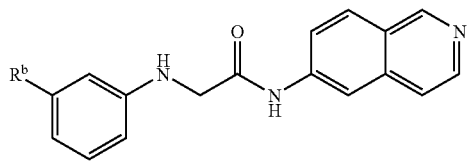

wherein $R^b$ is given separately for each example below in Table 2. The results are provided in terms activity at 50 μM as compared to control More active than control—+++

As active as control ++

Less active than control +

Inactive –

TABLE 2

| Example | R$^b$ | PTM Cell Assay |
|---------|-------|----------------|
| 1 | OCH2Ph | + |
| 2 | OMe | +++ |
| 3 | CN | +++ |
| 4 | CONHPh | +++ |
| 5 | Cl | ++ |
| 6 | H | ++ |
| 7 | OPh | +++ |
| 8 | SMe | +++ |
| 10 | CONH-m-Pyridine | +++ |
| 14 | COOMe | +++ |
| 15 | COPh | ++ |

EXAMPLE 28

An isoquinoline having the following structure was prepared as described above according to scheme 2 as set forth in Example 20.

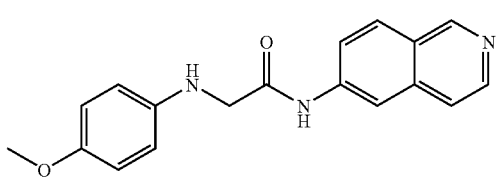

This isoquinoline was also tested using the PTM Cell Assay as described on reference Reference Example Two. The results using the scale above were as follows:
PTM Cell Assay +

EXAMPLE 29

An isoquinoline having the following structure was prepared as described above according to scheme 2 as set forth in Example 21.

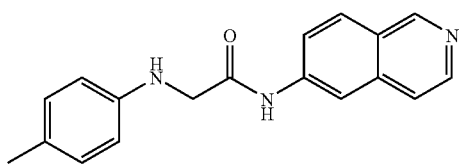

This isoquinoline was also tested using the PTM Cell Assay as described in Reference Example Two. The results using the scale above were as follows:
PTM Cell Assay ++

EXAMPLE 30

An isoquinoline having the following structure was prepared as described above according to scheme 2 as set forth in Example 22.

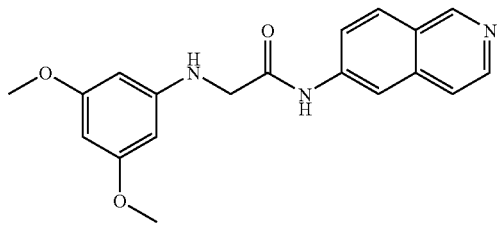

This isoquinoline was also tested using the PTM Cell Assay as described in Reference Example Two. The results using the scale above were as follows:
PTM Cell Assay −

EXAMPLE 31

An isoquinoline having the following structure was prepared as described above according to scheme 2 as set forth in Example 23.

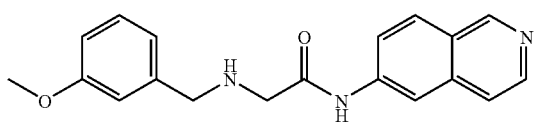

This isoquinoline was also tested using the PTM Cell Assay as described in reference Example Two. The results using the scale above were as follows:
PTM Cell Assay ++

Reference Example Three:

Pharmacological Activity for Glaucoma Assay.

Pharmacological activity for glaucoma can be demonstrated using assays designed to test the ability of the subject compounds to decrease intraocular pressure. Examples of such assays are described in the following reference, incorporated herein: C. Liljebris, G. Selen, B. Resul, J. Stern-schantz, and U. Hacksell, "Derivatives of 17-Phenyl-18,19, 20-trinorprostaglandin F$_2\alpha$ Isopropyl Ester: Potential Antiglaucoma Agents", *Journal of Medicinal Chemistry*, Vol. 38 (2) 1995, pp. 289-304.

EXAMPLE 32

Topical pharmaceutical compositions for lowering intraocular pressure are prepared by conventional methods and formulated as follows:

| Ingredient | Amount (wt %) |
|------------|---------------|
| Isoquinoline Derivative | 0.50 |
| Dextran 70 | 0.1 |
| Hydroxypropyl methylcellulose | 0.3 |
| Sodium Chloride | 0.77 |
| Potassium chloride | 0.12 |
| Disodium EDTA | 0.05 |
| Benzalkonium chloride | 0.01 |
| HCl and/or NaOH | pH 7.0-7.2 |
| Purified water | q.s. to 100% |

A compound according to this invention is used as the isoquinoline derivative. When the composition is topically administered to the eyes once daily, the above composition decreases intraocular pressure in a patient suffering from glaucoma.

EXAMPLE 33

Example 32 is repeated using N-Isoquinolin-6-yl-2-p-tolylamino-acetamide according to this invention. When administered as a drop 4 times per day, the above composition substantially decreases intraocular pressure and serves as a neuroprotective agent.

EXAMPLE 34

Example 32 is repeated using 2-(3-Benzoyl-phenylamino)-N-isoquinolin-6-yl-acetamide according to this invention. When administered as a drop twice per day, the above composition substantially decreases intraocular pressure.

EXAMPLE 35

Example 32 is repeated using 3-[(Isoquinolin-6-ylcarbamoylmethyl)-amino]-N-pyridin-3-yl-benzamide according to this invention. When administered as a drop twice per day, the above composition substantially decreases allergic symptoms and relieves dry eye syndrome.

EXAMPLE 36

Example 32 is repeated using a 4-[(Isoquinolin-6-ylcarbamoylmethyl)-amino]-N-pyridin-4-yl-benzamide according to this invention. When administered as a drop as needed, the above composition substantially decreases hyperemia, redness and ocular irritation.

EXAMPLE 37

Example 32 is repeated using N-(isoquinolin-6-yl)-2-(4-methoxyphenylamino)acetamide according to this invention. When administered as a drop 4 times per day, the above composition substantially decreases intraocular pressure and serves as a neuroprotective agent.

EXAMPLE 38

Example 32 is repeated using N-(isoquinolin-6-yl)-2-(4-(methylthio)phenylamino)acetamide according to this invention. When administered as a drop twice per day, the above composition substantially decreases intraocular pressure.

EXAMPLE 39

Example 32 is repeated using phenyl 3-(2-(isoquinolin-6-ylamino)-2-oxoethylamino)benzoate according to this invention. When administered as a drop twice per day, the above composition substantially decreases allergic symptoms and relieves dry eye syndrome.

EXAMPLE 40

Example 32 is repeated using phenyl 4-(2-(isoquinolin-6-ylamino)-2-oxoethylamino)benzoate according to this invention. When administered as a drop as needed, the above composition substantially decreases allergic symptoms

EXAMPLE 41

Example 32 is repeated using N-(isoquinolin-6-yl)-2-(3-(methylthio)phenylamino)acetamide according to this invention. When administered as a drop as needed, the above composition substantially decreases hyperemia, redness and ocular irritation.

EXAMPLE 42

Example 32 is repeated using N-(2-fluorophenyl)-4-(2-(isoquinolin-6-ylamino)-2-oxoethylamino)benzamide according to this invention. When administered as a drop twice a day or as needed, the above composition substantially decreases intraocular pressure.

EXAMPLE 43

Example 32 is repeated using N-(2-fluorophenyl)-2-(2-(isoquinolin-6-ylamino)-2-oxoethylamino)benzamide according to this invention. When administered as a drop twice a day or as needed, the above composition substantially decreases intraocular pressure.

EXAMPLE 44

Example 32 is repeated using N-(isoquinolin-6-yl)-2-(3-sulfamoylphenylamino)acetamide according to this invention. When administered as a drop twice a day or as needed, the above composition substantially decreases intraocular pressure.

EXAMPLE 45

Example 32 is repeated using N-(isoquinolin-6-yl)-2-(4-sulfamoylphenylamino)acetamide according to this invention. When administered as a drop twice a day or as needed, the above composition substantially decreases pressure.

EXAMPLE 46

Example 32 is repeated using N-(isoquinolin-6-yl)-2-(4-(N-methylsulfamoyl)phenylamino)acetamide according to this invention. When administered as a drop twice a day or as needed, the above composition substantially decreases intraocular pressure.

While the invention has been described in detail and with reference to specific embodiments thereof, it will be apparent to one skilled in the art that various changes and modifications can be made without departing from the spirit and scope of the invention.

What is claimed is:

1. A compound according to Formula (I):

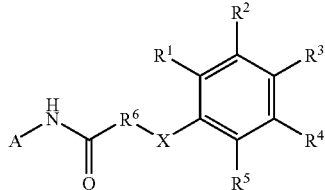

wherein A is an unsubstituted isoquinoline radical; wherein the isoquinoline radical has the formula

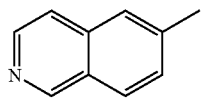

$R^1$, $R^2$, $R^3$, $R^4$, and $R^5$ are, independently, hydrogen; halogen; $C_1$-$C_8$ alkyl; alkoxy; phenoxy, —$OR^7$; amino; nitro; cyano; aryl; $C_1$-$C_4$ alkylaryl; heteroaryl; $C_1$-$C_4$ alkyl heteroaryl; carbonylamino; thioalkyl; sulfonyl; sulfonylamino; acyl; or carboxyl;

$R^7$ is $C_1$-$C_4$ alkyl, aryl, heteroaryl, $C_1$-$C_4$ alkyl aryl or $C_1$-$C_4$ alkyl heteroaryl;

X is

and $R^6$ is $CH_2$ or $CH(C_1$-$C_4$ alkyl).

2. A compound according to claim 1 wherein $R^1$, $R^2$, $R^3$, $R^4$, and $R^5$ are not phenoxy.

3. A compound according to claim 2 wherein X is

4. A compound according to claim 3 wherein $R^1$, $R^3$, and $R^5$ are hydrogen.

5. A compound according to claim 3 wherein $R^1$, $R^2$, $R^3$, and $R^5$ are hydrogen and $R^4$ is —O—$R^7$.

6. A compound according to claim 3 wherein $R^4$ is carbonylamino, sulfylamino, acyl or carboxyl.

7. A compound according to claim 3 wherein $R^1$, $R^2$, and $R^5$ are H and one of $R^3$ and $R^4$ is carbonylamino, sulfylamino, acyl or carboxyl.

8. A compound according to Formula II:

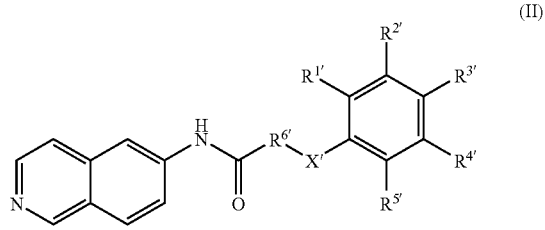

wherein $R^{1'}$, $R^{2'}$, $R^{3'}$, $R^{4'}$, and $R^{5'}$ are, independently, hydrogen; halogen; unsubstituted $C_1$-$C_4$ alkyl; amino; nitro; cyano; carbonylamino; alkoxy; —O—$R^{7'}$; sulfonylamino; carboxyl; acyl; or thioalkyl;

$R^{7'}$ is $C_1$-$C_4$ alkyl, aryl, heteroaryl, $C_1$-$C_4$ alkyl aryl or $C_1$-$C_4$ alkyl heteroaryl;

X' is

and $R^{6'}$ is $CH_2$ or $CH(C_1$-$C_4$ alkyl).

9. A compound according to claim 8 wherein X' is

10. A compound according to claim 8 wherein $R^{1'}$, $R^{2'}$, $R^{3'}$, and $R^{5'}$ are hydrogen and $R^{4'}$, is —O—$R^{7'}$.

11. A compound according to claim 8 wherein $R^{4'}$ is carbonylamino, sulfylamino, acyl or carboxyl.

12. A compound according to claim 11 wherein $R^{4'}$ is carbonylamino, and the carbonylamino is C(O)NHphenyl, C(O)NH-m-pyridyl, C(O)NH-o-pyridyl, C(O)NH-p-pyridyl, C(O)NH$_2$, or C(O)NHCH$_3$.

13. A compound according to claim 8 wherein $R^{1'}$, $R^{2'}$, and $R^{5'}$ are H and one of $R^{3'}$ and $R^{4'}$ is carbonylamino, sulfylamino, acyl or carboxyl.

14. A compound according claim 9 wherein $R^{2'}$ or $R^{4'}$ is —O—$R^{7'}$.

15. A compound according to claim 14 wherein $R^{7'}$ is methyl, ethyl, phenyl, benzyl, propyl or isopropyl.

16. A compound according to Formula III:

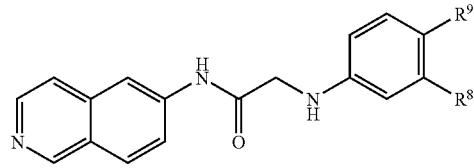

wherein $R^8$ and $R^9$ are independently hydrogen; halogen; unsubstituted $C_1$-$C_4$ alkyl; substituted $C_1$-$C_4$ alkyl; amino; nitro; cyano; carbonylamino; alkoxy; phenoxy, benzyloxy, —O—$R^{10}$; sulfonylamino; carboxyl; acyl; or thioalkyl; and $R^{10}$ is unsubstituted $C_1$-$C_4$ alkyl; substituted $C_1$-$C_4$ alkyl;, substituted aryl, heteroaryl, substituted heteroaryl, $C_1$-$C_4$ alkaryl or $C_1$-$C_4$ alkheteroaryl.

17. A compound according to claim 16 wherein $R^8$ is carbonylamino, a carboxyl, a sulfonyl amino, a cyano, or an acyl moiety, and $R^9$ is selected from H, methyl, cyano, or halogen.

18. A compound according to claim 17 wherein $R^8$ is the carbonylamino, and the carbonylamino is C(O)NHphenyl, C(O)NH-m-pyridyl, C(O)NH-o-pyridyl, C(O)NH-p-pyridyl, C(O)NH$_2$, and C(O)NHCH$_3$.

19. A compound according to claim 17 wherein $R^8$ is the carboxyl and the carboxyl is C(O)O phenyl, C(O)O-m-pyridyl, C(O)O-o-pyridyl, C(O)O-p-pyridyl, C(O)NH$_2$, or C(O)OCH$_3$.

20. A compound according to claim 17 wherein $R^8$ is the sulfonyl amino, and the sulfonyl amino is S(O)2NHphenyl, S(O)2NH-m-pyridyl, S(O)2NH-o-pyridyl, S(O)2NH-p-pyridyl, S(O)2NH$_2$, or S(O)2NHCH$_3$.

21. A compound according to claim 16 wherein $R^9$ is a carbonylamino, a carboxyl, a sulfonyl amino, a cyano, or an acyl moiety, and $R^8$ is H, methyl, cyano, or halogen.

22. A compound according to claim 16 wherein $R^8$ is alkoxy, phenoxy, benzyloxy, or —O—$R^{10}$ and $R^9$ is H, methyl, cyano, or halogen.

23. A compound according to claim 16 wherein $R^8$ and $R^9$ are not phenoxy.

24. A pharmaceutical composition comprising:
   a) an isoquinoline derivative having the structure

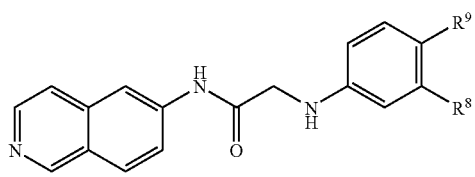

wherein $R^8$ and $R^9$ are independently hydrogen; halogen; unsubstituted $C_1$-$C_4$ alkyl; substituted $C_1$-$C_4$ alkyl; amino; nitro; cyano; carbonylamino; alkoxy; phenoxy, benzyloxy, —O—$R^{10}$; sulfonylamino; carboxyl; acyl; or thioalkyl; and $R^{10}$ is unsubstituted $C_1$-$C_4$ alkyl; substituted $C_1$-$C_4$ alkyl;, substituted aryl, heteroaryl, substituted heteroaryl, $C_1$-$C_4$ alkaryl or $C_1$-$C_4$ alkheteroaryl; and
   b) a carrier.

25. The composition of claim 24, wherein the carrier is selected from the group consisting of systemic and topical carriers.

26. A compound selected from the following:

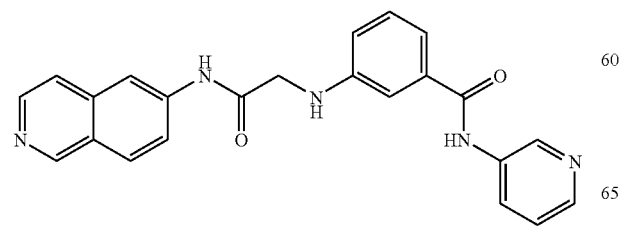

-continued

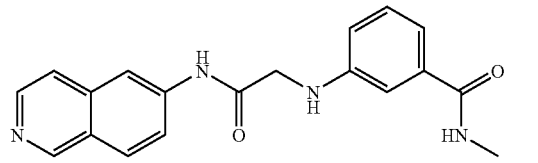

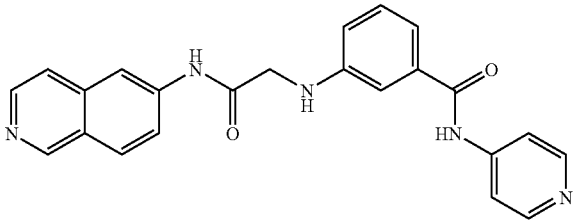

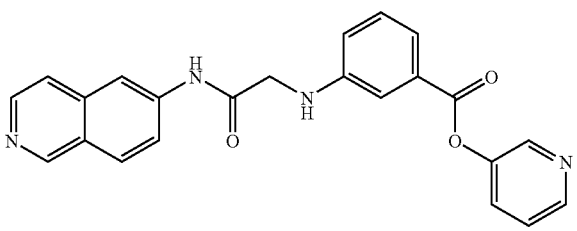

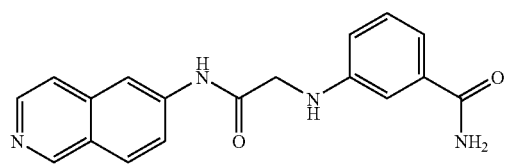

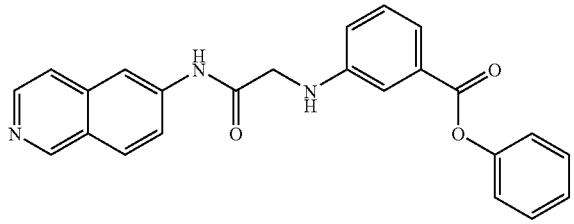

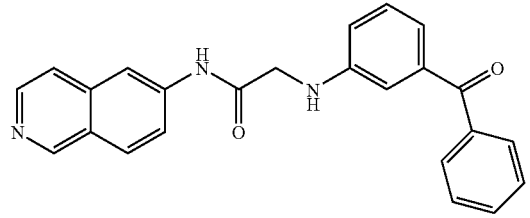

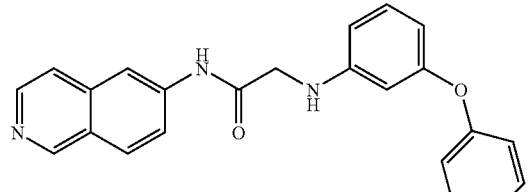

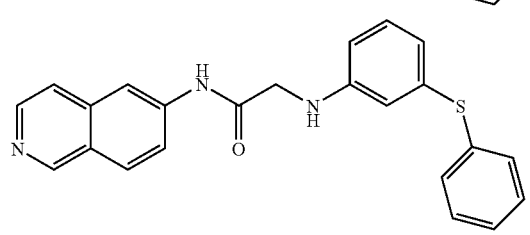

-continued
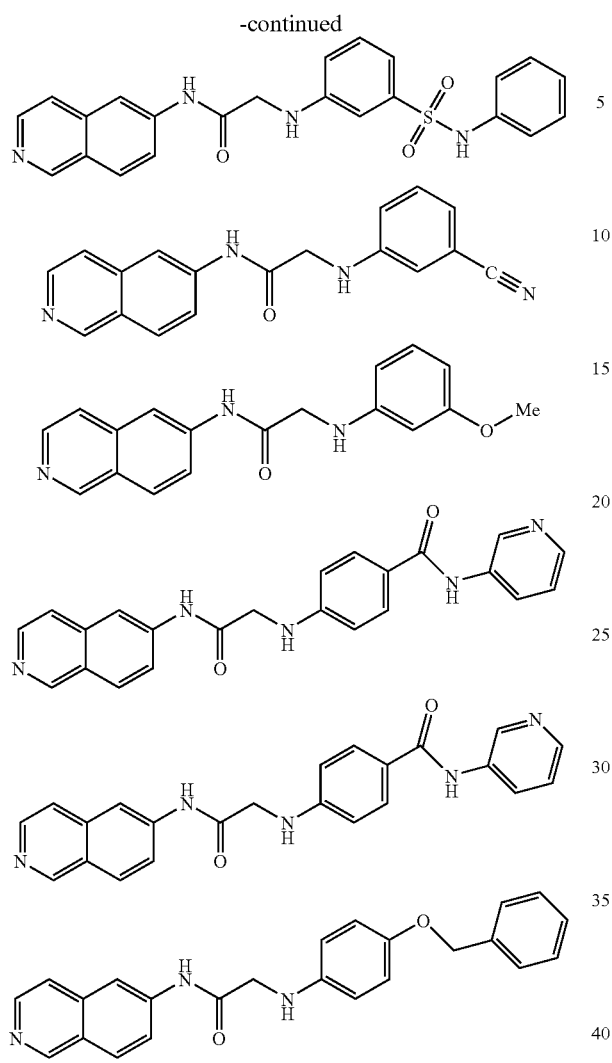
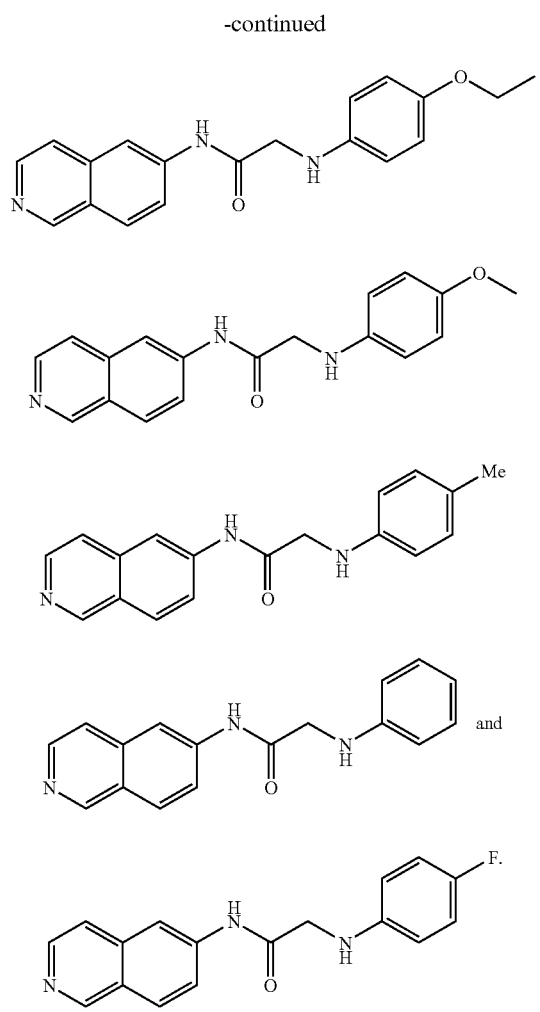
* * * * *

UNITED STATES PATENT AND TRADEMARK OFFICE
CERTIFICATE OF CORRECTION

PATENT NO. : 7,470,787 B2
APPLICATION NO. : 11/485172
DATED : December 30, 2008
INVENTOR(S) : Mitchell A. deLong et al.

Page 1 of 1

It is certified that error appears in the above-identified patent and that said Letters Patent is hereby corrected as shown below:

Column 25, line 22, after the word "for"
replace the word [[quinolines]] with isoquinolines.

Signed and Sealed this

First Day of September, 2009

David J. Kappos
*Director of the United States Patent and Trademark Office*